United States Patent
Hamilton et al.

(10) Patent No.: US 9,483,616 B2
(45) Date of Patent: Nov. 1, 2016

(54) SYSTEMS AND METHODS FOR COLLECTING INFORMATION AT AN EMERGENCY VEHICLE

(75) Inventors: Richard Hamilton, Oceanside, CA (US); Edward Kerkow, Tenafly, NJ (US)

(73) Assignee: ACS State & Local Solutions, Inc., Teaneck, NJ (US)

( * ) Notice: Subject to any disclaimer, the term of this patent is extended or adjusted under 35 U.S.C. 154(b) by 1971 days.

(21) Appl. No.: 10/437,997

(22) Filed: May 15, 2003

(65) Prior Publication Data

US 2003/0233254 A1 Dec. 18, 2003

Related U.S. Application Data

(60) Provisional application No. 60/384,105, filed on May 31, 2002.

(51) Int. Cl.
*G06F 19/00* (2011.01)
*G06Q 10/10* (2012.01)
(Continued)

(52) U.S. Cl.
CPC .......... *G06F 19/328* (2013.01); *G06F 19/322* (2013.01); *G06F 19/3418* (2013.01); *G06Q 10/10* (2013.01); *G06Q 20/102* (2013.01); *G06Q 30/04* (2013.01); *G06Q 50/22* (2013.01); *G06F 19/3487* (2013.01)

(58) Field of Classification Search
CPC ...... G06Q 50/22; G06Q 50/24; G06Q 40/08; G06Q 10/10; G06F 19/322
USPC ........................................................ 705/2–4
See application file for complete search history.

(56) References Cited

U.S. PATENT DOCUMENTS 4,491,725 A * 1/1985 Pritchard .......................... 705/2
4,764,870 A 8/1988 Haskin .......................... 364/415
(Continued)

FOREIGN PATENT DOCUMENTS

WO    WO 00/49549 A1    8/2000    ............. G06F 17/60

OTHER PUBLICATIONS

Dalcher, Lessons for the future: safety critical systems, Mar. 7, 1999, Engineering of Computer-Based Systems, 1999. Proceedings. ECBS '99. IEEE Conference and Workshop on, p. 281-293.*

(Continued)

*Primary Examiner* — Tran Nguyen
(74) *Attorney, Agent, or Firm* — Finnegan, Henderson, Farabow, Garrett & Dunner, LLP

(57) ABSTRACT

A method for collecting information at a vehicle, such as an emergency vehicle, involves receiving at the vehicle a request regarding a patient. The method further involves collecting information on the patient using a mobile computer at the vehicle. The method also involves transmitting the patient information as an electronic file from the mobile computer to a hospital over a network. As part of this method, billing information concerning the patient may be collected. Additionally, a method for processing billing information concerning a patient involves collecting billing information regarding the patient from a mobile computer at a vehicle over a network. The method further involves classifying a service provided to the patient in at least one billing category based on the billing information. In addition, the method further involves generating a bill for the patient based on the billing information.

32 Claims, 25 Drawing Sheets

(51) Int. Cl.
*G06Q 20/10* (2012.01)
*G06Q 30/04* (2012.01)
*G06Q 50/22* (2012.01)

(56) References Cited

U.S. PATENT DOCUMENTS

| | | | | |
|---|---|---|---|---|
| 4,809,697 | A | | 3/1989 | Causey, III et al. .... 128/419 PT |
| 5,005,126 | A | | 4/1991 | Haskin .................... 364/413.13 |
| 5,065,315 | A | | 11/1991 | Garcia .................... 364/413.01 |
| 5,482,050 | A | | 1/1996 | Smokoff et al. ............. 128/710 |
| 5,493,694 | A | * | 2/1996 | Vlcek et al. ................... 455/521 |
| 5,586,556 | A | | 12/1996 | Spivey et al. ................ 128/697 |
| 5,619,991 | A | * | 4/1997 | Sloane .......................... 600/300 |
| 5,730,146 | A | | 3/1998 | Itil et al. ....................... 128/732 |
| 5,748,907 | A | | 5/1998 | Crane .......................... 395/202 |
| 5,832,450 | A | | 11/1998 | Myers et al. ..................... 705/3 |
| 5,987,519 | A | | 11/1999 | Peifer et al. .................. 709/230 |
| 6,032,261 | A | | 2/2000 | Hulyalkar .................... 713/400 |
| 6,065,119 | A | | 5/2000 | Sandford, II et al. ........ 713/200 |
| 6,093,019 | A | | 7/2000 | Morandi et al. ................ 433/29 |
| 6,112,224 | A | | 8/2000 | Peifer et al. .................. 709/202 |
| 6,117,073 | A | * | 9/2000 | Jones .................. G06F 19/327 600/300 |
| 6,283,761 | B1 | * | 9/2001 | Joao ................... 434/236 |
| 6,381,577 | B1 | | 4/2002 | Brown ............................. 705/2 |
| 6,430,496 | B1 | * | 8/2002 | Smith et al. .................. 701/117 |
| 7,181,505 | B2 | * | 2/2007 | Haller et al. .................. 709/219 |
| 7,233,905 | B1 | * | 6/2007 | Hutton et al. .................... 705/2 |
| 7,249,036 | B2 | * | 7/2007 | Bayne ............................. 705/2 |
| 2001/0051787 | A1 | | 12/2001 | Haller et al. ..................... 604/66 |
| 2002/0004729 | A1 | * | 1/2002 | Zak et al. ......................... 705/3 |
| 2002/0032583 | A1 | | 3/2002 | Joao ................................. 705/2 |
| 2002/0169638 | A1 | | 11/2002 | Rodriguez-Cue ................ 705/3 |
| 2005/0060198 | A1 | * | 3/2005 | Bayne ............................. 705/2 |
| 2005/0113996 | A1 | * | 5/2005 | Pillar et al. ..................... 701/36 |
| 2007/0203742 | A1 | * | 8/2007 | Jones et al. ...................... 705/2 |

OTHER PUBLICATIONS

Breant, Interfacing aspects between the picture archiving communications systems, radiology information systems, and hospital information systems, vol. 6, No. 2 / May 1993, Journal of Digital Imaging.*

Breant, Interfacing aspects between the picture archiving communications systems, radiology information systems, and hospital imformation systems, vol. 6, No. 2 / May 1993, Journal of Digital Imaging.*

Holzman, Computer-Human Interface Solutions for Emergency Medical Care, May 1999, ACM, vol. 6, Issue 3, p. 13-24.*

Bonsor, K., "How E-ZPass Works" (visited Jun. 27, 2003) {http://www.hotstuffworks.com/e-pass.htm/printable}, 4 pages.

"SafetyPAD: for EMS: An innovative, comprehensive, pre-hospital information management solution" (visited Jun. 27, 2003) {http://www.safetypad.com/products.htm}, 6 pages.

"SafetyPAD: Overview (innovation that works)" (visited Jun. 27, 2003) {http://www.safetypad.com/overvw.htm}, 8 pages.

"SafetyPAD: Features and Benefits" (visited Jun. 27, 2003) {http://www.safetypad.com/feat.htm}, 6 pages.

* cited by examiner

| | |
|---|---|
| ① PATIENT INFORMATION | 🚑 AMBULANCE STATUS [ETA - UNKNOWN] |
| 1 of 1; Smith, John; M, 43yr old | Medic 19 at Scene @ 12:17 |
| ▲ Hx PRESENT<br><br>CAUSE UNKNOWN<br>COMPLAINT ABDOMINAL PAIN<br>SYMPTOMS DENIES LOSS OF CONS.<br>SYMPTOMS WEAKNESS, DIZZINESS | ▼ Hx PAST<br><br>ALLERGIES NONE<br>MEDS LASIX<br>PREEXIST CARDIAC |
| + CARE EVENTS<br><br>12:20 VITALS 92 26 140/96<br>12:23:34 OXYGEN<br>12:25:45 CARDIAC MONITOR<br>12:28 NORMAL SALINE | |
| FINDINGS<br><br>LOC ALERT<br>AIRWAY PATENT<br>BREATHING NON-LABORED<br>CIRCULATION PULSE PRESENT<br>GCS 15<br>EYES<br>SKIN PALE, MOIST<br>GENERAL WEAK SWEATING | 📎 ✂<br>No attachments available<br><br>_Patient List_<br>_Chat / Query_<br>_Print_ |

| Patient ID /710 | Name /720 | Present Hx /730 | Past Hx /740 | Findings /750 | Address /760 | Type of Coverage /780 |
|---|---|---|---|---|---|---|
| 1 | J. Smith | Abdominal Pain | Allergic to Pet Dander | Alert | 1 Golf St. Phoenix, AZ | Insurance |
| 2 | K. Paul | Dizziness | None | Dizzy | 1 Lakeshore St. Denver, CO | Medicare |
| 3 | L. Jones | Head Trauma | Stomach Ulcer | Unconscious | Unknown | Unknown |
| 4 | P. Hu | Bleeding Arm | None | Dizzy | 3 Soccer Blvd. Palm Beach, FL | Self-Pay |

FIG. 7

| Patient ID ⟋810 | Name ⟋820 | Address ⟋830 | Service Rendered ⟋840 | Name of Physician ⟋850 | Bill Status ⟋860 | Payment Status ⟋870 | Type of Coverage ⟋880 | Code ⟋890 |
|---|---|---|---|---|---|---|---|---|
| 1 | J. Smith | 1 Golf St. Phoenix, AZ | Transport to Hospital | — | Sent | Paid | Insurance | XYZ |
| 2 | K. Paul | 1 Lakeshore St. Denver, CO | Transport to Hospital Meds. | N. Kumar | Processing | N/A | Medicare | ABC |
| 3 | L. Jones | Unknown | Transport to Hospital ICU | P. O'Connell | Sent | Unpaid | Unknown | P2R |
| 4 | P. Hu | 3 Soccer Blvd. Palm Beach, FL | Bandage First Aid | — | Sent | Paid | Self-Pay | XYZ |

FIG. 8

SYSTEMS AND METHODS FOR COLLECTING INFORMATION AT AN EMERGENCY VEHICLE

This application claims priority under 35 U.S.C. §119 based on U.S. Provisional Application No. 60/384,105, filed May 31, 2002, the complete disclosure of which is incorporated herein by reference.

FIELD OF THE INVENTION

The present invention generally relates to the field of collecting and processing information. More particularly, the invention relates to systems and methods for collecting information at an emergency vehicle, including medical information and billing information.

BACKGROUND AND MATERIAL INFORMATION

Traditional emergency medical information systems involve the use of paper and pen to collect information at an emergency vehicle. Collection of information in that manner results in several disadvantages. First, such systems are expensive because of the need for the manual data entry of the collected information. This is because the labor costs are increasing faster than other inputs. Moreover, to ensure correctness of the data entry, the emergency vehicle personnel may have to review the entered data.

Second, collection of information using a paper and pen results in a greater possibility of errors being introduced because of, for example, the risk of data entry personnel's inability to properly transcribe handwritten notes. Moreover, such handwritten notes may be lost thereby in complete loss of information collected at the emergency vehicle.

Third, errors in recording and transcribing information may expose the operator of the emergency vehicle to legal liability. Liability may also result, for example, where all of the appropriate information may not have been gathered. Further, illegible writing may result in wrong diagnosis and treatment by the downstream medical personnel.

Moreover, lack of electronic information also results in an inability to provide such critical information to downstream medical personnel. For example, an emergency vehicle that can not transmit paper based information may not be able to get this information to the hospital to which the emergency vehicle is headed, ahead of time.

Further, emergency personnel at an emergency vehicle also need to gather billing information. Such information is typically collected using pen and paper and sent via postal mail to a billing center. The billing information is then data entered and subsequently a bill may be sent via postal mail to the patient. Handling of billing information in this manner results in delays and errors. For example, services or medications administered to a patient may not have been recorded or coded properly resulting in billing for the wrong services or medications. For this reason, billing information is not gathered at the emergency vehicles.

Moreover, paper-based processing of the billing information further results in delays in processing the bills. These delays further impact the ability of a service provider, such as a city hospital to collect payments. Typically, such delays and errors in billing information may cost a city or a municipality millions of dollars in lost revenue.

Similarly paper-based systems to notify patients with outstanding bills result in low recovery of outstanding bills. Additionally, such systems are expensive to operate.

Accordingly, there is a need for improved systems and methods for collecting information at an emergency vehicle, including medical information and billing information.

SUMMARY

Apparatus and methods consistent with embodiments of the present invention provide systems and methods for collecting information at an emergency vehicle, including billing information and medical information. The systems and methods further relate to processing the collected medical and billing information.

According to one embodiment of the invention, a method for collecting medical and billing information about a patient at an emergency vehicle is provided. The method may involve receiving a call at a dispatch service about the patient. It may further include sending a dispatch order from the dispatch service to the emergency vehicle based on the call and receiving at the emergency vehicle the dispatch order about the patient from the dispatch service. The method may further include collecting medical information about the patient using a mobile computer at the emergency vehicle and collecting billing information about the patient using the mobile computer at the emergency vehicle. Further, the method may include merging the collected medical and billing information at the emergency vehicle. In addition, the method may include transmitting the merged medical and billing information as an electronic file from the mobile computer at the emergency vehicle to at least one of a medical facility and a billing service.

According to another embodiment of the invention, a method for collecting information about a patient at a vehicle, comprising is provided. The method may include receiving at the vehicle a request regarding the patient. The method may further include collecting medical and billing information about the patient using a mobile computer at the vehicle. Also, the method may include synchronizing the collected medical and billing information from the mobile computer to a vehicle computer. In addition, the method may include transmitting the collected medical and billing information as an electronic file from the vehicle computer to at least one of a medical facility and a billing service over a network.

According to yet another embodiment of the invention, a method for collecting medical and billing information about a patient at an emergency vehicle is provided. The method may include receiving at the emergency vehicle a dispatch order about the patient from the dispatch service. The method may further include collecting medical information about the patient using a mobile computer at the emergency vehicle and collecting billing information about the patient using the mobile computer at the emergency vehicle. Moreover, the method may include merging the collected medical and billing information at the emergency vehicle. Further, the method may include synchronizing the collected medical and billing information from the mobile computer to a vehicle computer. In addition, the method may include transmitting the merged medical and billing information as an electronic file from the vehicle computer to at least one of a medical facility and a billing service.

According to still another embodiment of the invention, a method for processing medical and billing information about a patient at an emergency vehicle is provided. The method may include collecting information about the patient at the emergency vehicle, wherein the information includes medical and billing information. Additionally, the method may include classifying a service provided to the patient in at least one medical category for the medical information. The method may further include transmitting the medical information as an electronic file to medical facility over a network. Further, the method may include classifying a service provided to the patient in at least one billing category for the billing information. In addition the method may include transmitting the billing information as an electronic file to a bill processing center over a network.

According to another embodiment of the invention, a method for processing medical information about a patient from an emergency vehicle to a medical facility is provided. The method may include collecting medical information about the patient using a mobile computer at the emergency vehicle. Also, the method may include classifying a service provided to the patient in at least one medical category for the medical information. Further, the method may include synchronizing the collected medical information from the mobile computer to a vehicle computer. In addition, the method may include transmitting the medical information from the vehicle computer as an electronic file to a medical facility over a network.

According to yet another embodiment of the invention a method for processing billing information about a patient at an emergency vehicle is provided. The method may include collecting billing information about the patient using a mobile computer at the emergency vehicle. The method may further include classifying a service provided to the patient in at least one billing category for the billing information. Further, it may include synchronizing the collected billing information from the mobile computer to a vehicle computer. In addition, the method may include transmitting the billing information from the vehicle computer as an electronic file to a bill processing center over the network.

Both the foregoing general description and the following detailed description are exemplary and are intended to provide further illustration and explanation of the embodiments of the invention as claimed.

BRIEF DESCRIPTION OF THE DRAWINGS

The accompanying drawings, which are incorporated in and constitute a part of this specification, illustrate various embodiments and aspects of the present invention. In the drawings:

FIG. 4 is a schematic diagram illustrating an exemplary electronic file corresponding to medical information for transmission from a mobile computer to a medical facility consistent with the methods and systems of the present invention;

FIG. 7 is a schematic diagram illustrating exemplary information stored in a patient database consistent with the methods and systems of the present invention;

FIG. 8 is a schematic diagram illustrating exemplary information stored in a billing database consistent with the methods and systems of the present invention;

DETAILED DESCRIPTION OF THE EMBODIMENTS

Methods and systems consistent with embodiments of the present invention relate to collecting information at an emergency vehicle, including medical information and billing information. The systems and methods further relate to processing the collected medical and billing information.

Figure 1A:
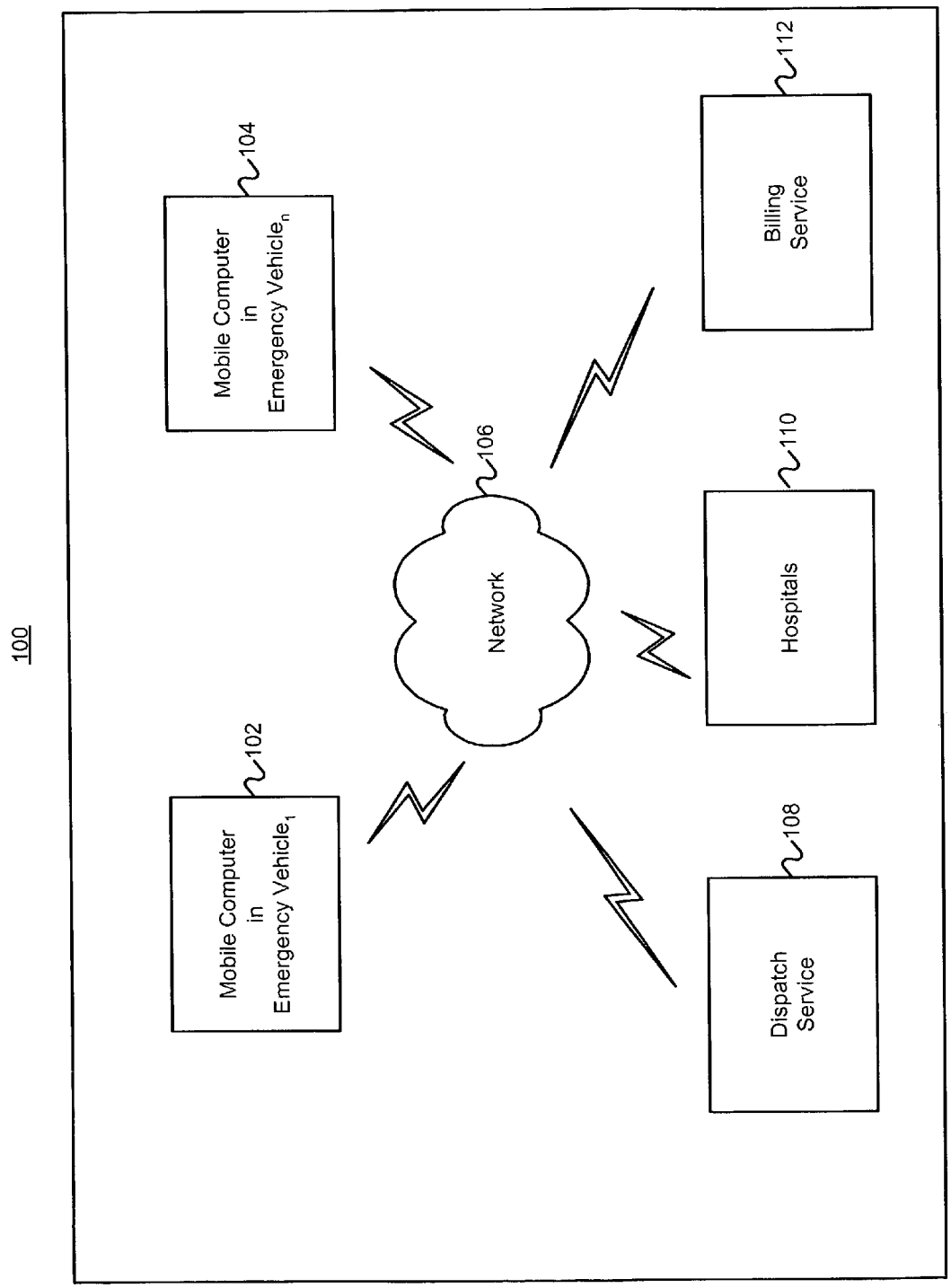
FIG. 1A illustrates an exemplary system environment, consistent with methods and systems of the present invention.

As shown in FIG. 1A, an exemplary system environment 100 may include a mobile computer in an emergency vehicle, 102 and a mobile computer in an emergency vehicle$_n$ 104 connected via a network 106 to a dispatch service 108, hospital(s) 110, and a billing service 112. Using network 106, any of the mobile computers in any of the emergency vehicles may communicate with the dispatch service, any of the hospitals, and/or the billing service. Examples of networks that may be used to exchange information among the various components of FIG. 1 include networks such as the Internet, telephony networks, private networks, virtual private networks, local area networks, metropolitan area networks, wide area networks, ad hoc networks, state networks, frame-relay networks, or any other mechanism for permitting communication between remote sites, regardless of whether the connection is wired or wireless. Thus, the present invention can be used in any environment where information may be exchanged by any means among the various components, including, for example the mobile computers in the emergency vehicles and the hospitals. Also, although FIG. 1 depicts only one dispatch service and one billing service, there may be more than one of each of these.

Figure 1B:
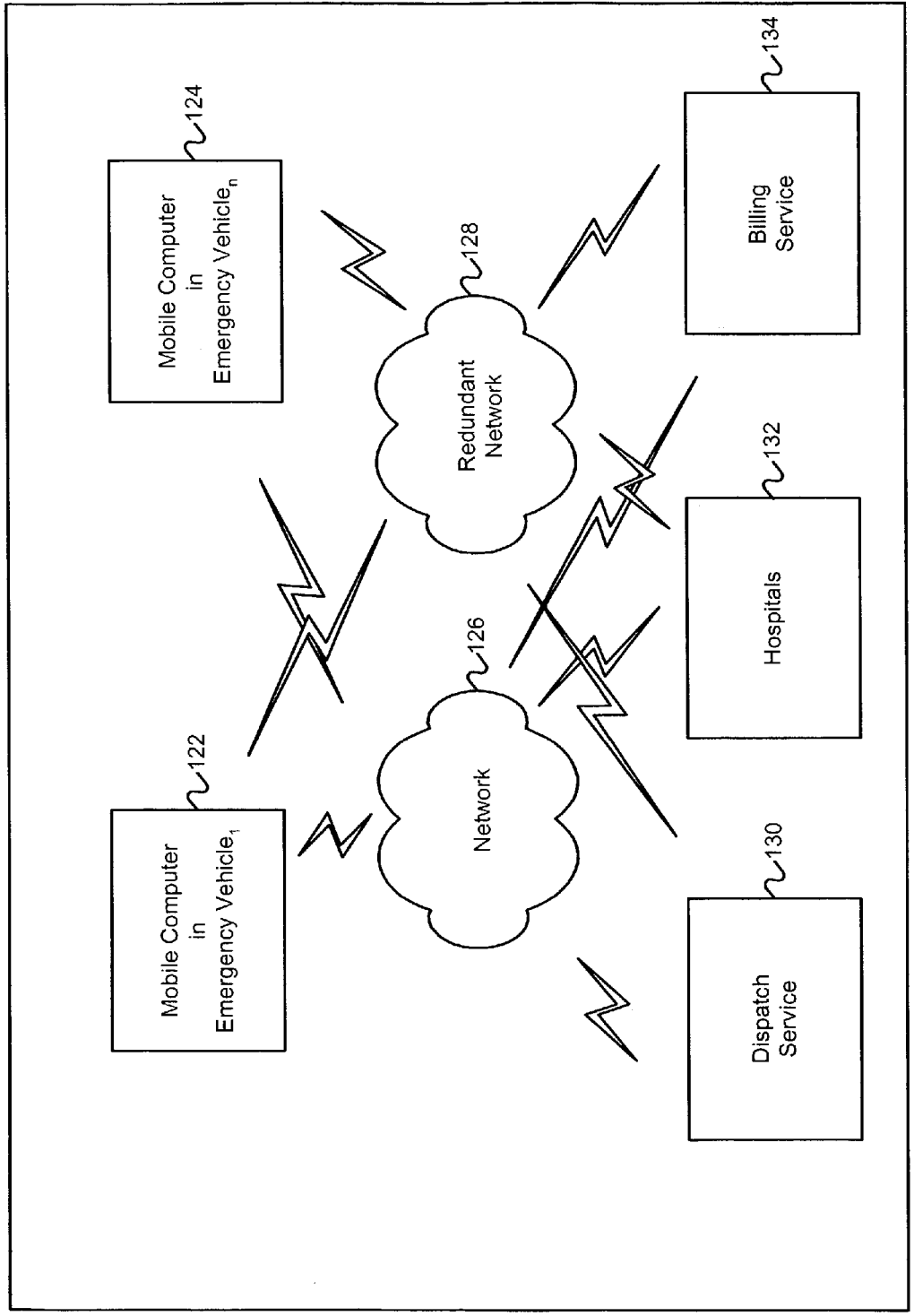
FIG. 1B illustrates another exemplary system environment, consistent with methods and systems of the present invention.

As shown in FIG. 1B, another exemplary system environment 120 may include a mobile computer in an emergency vehicle 122, and a mobile computer in another emergency vehicle$_n$ 124 connected via a network 126 and a redundant network 128 to a dispatch service 130, hospitals 132, and a billing service 134. Using network 126 any of the mobile computers, in any of the emergency vehicles, may communicate with the dispatch service, any of the hospitals, and/or the billing service. Similarly, using the redundant network 128, any of the emergency vehicles may communicate with the dispatch service, any of the hospitals, and/or the billing service. The examples of networks that may be used to exchange information may be any of the networks noted above with respect to FIG. 1A. In a particular embodiment consistent with the present invention, network 126 may be comprised of a Motorola RF network. In an exemplary embodiment, redundant network 128 may comprise a wide area network.

Figure 1C:
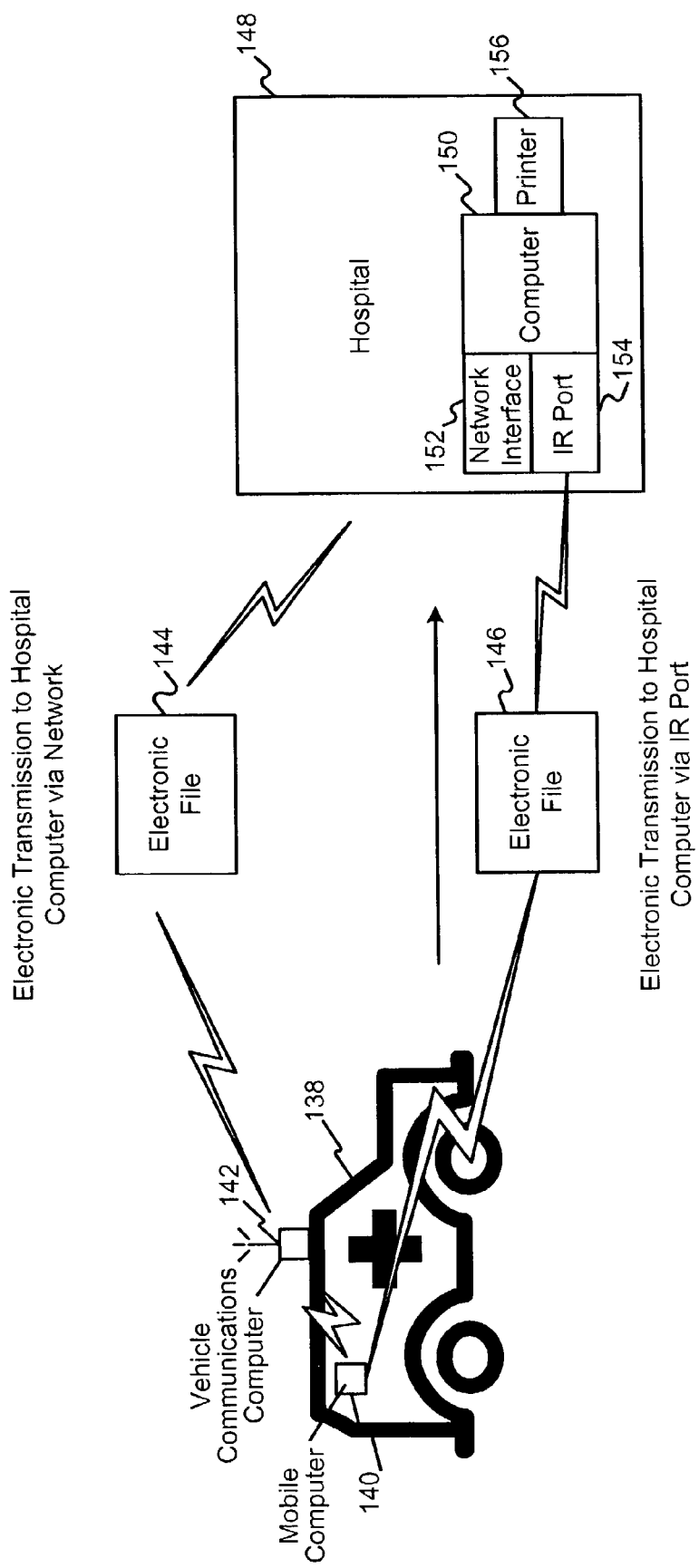
FIG. 1C is a schematic diagram illustrating transmission of information from a vehicle to a hospital consistent with methods and systems of the present invention.

Referring now to FIG. 1C, electronic transmission of information from a vehicle to a hospital computer via a network, as shown. Thus, for example, an electronic file 144 may be transmitted from a vehicle 138 to a hospital 148. Hospital 148 may have a computer 150 connected to a network interface 152, an IR port 154, and a printer 156. In one embodiment, an electronic file 144 may be transmitted from a vehicle communications computer 142 to computer 150 through network interface 152. In another embodiment, an electronic file 146 may be transmitted from a mobile computer 140 (located in vehicle 138) to computer 150 via IR port 154. Although FIG. 1C shows only two ways of transmitting an electronic file from a vehicle to a hospital, other arrangements or other ways of transmitting a file from a vehicle to hospital may also be used. For example, an electronic file may be transmitted from vehicle communications computer 142 which may then transmit the electronic file to the hospital computer 150 through network interface 152. In one embodiment, the electronic file (for example electronic file 146) may be transmitted from the vehicle to the hospital using Motorola's RF network.

Figure 1D:
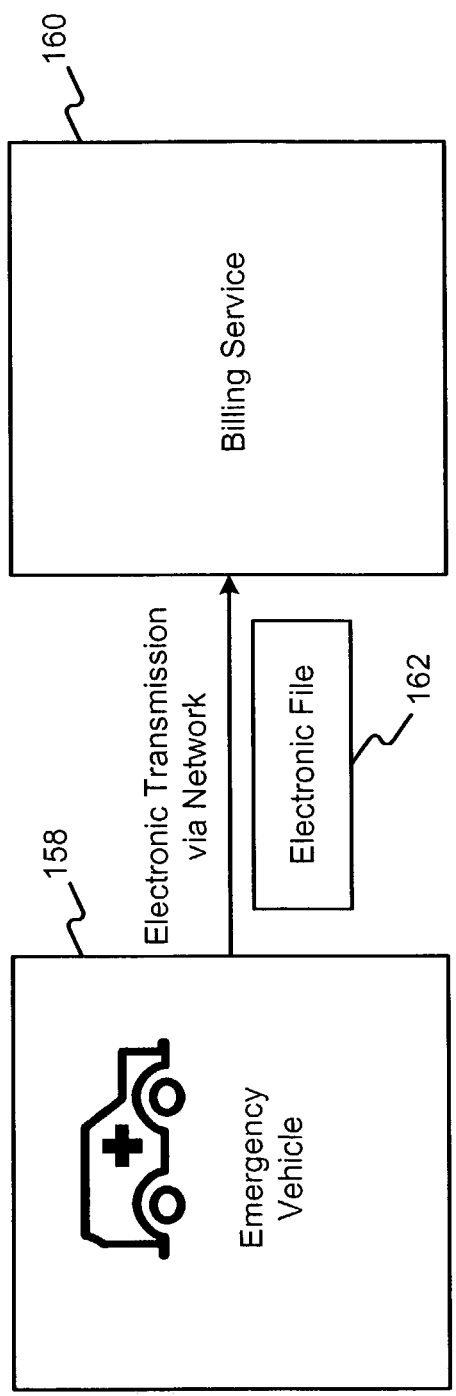
FIG. 1D is a schematic diagram illustrating transmission of information from a vehicle to a billing service consistent with methods and systems of the present invention.

Referring now to FIG. 1D, electronic transmission of an electronic file 162 from an emergency vehicle 158 to a billing service 160 is shown. As discussed above with respect to FIG. 1C, the transmission of electronic file 162 may occur via an infrared IR port or through a network interface.

Figure 1E:
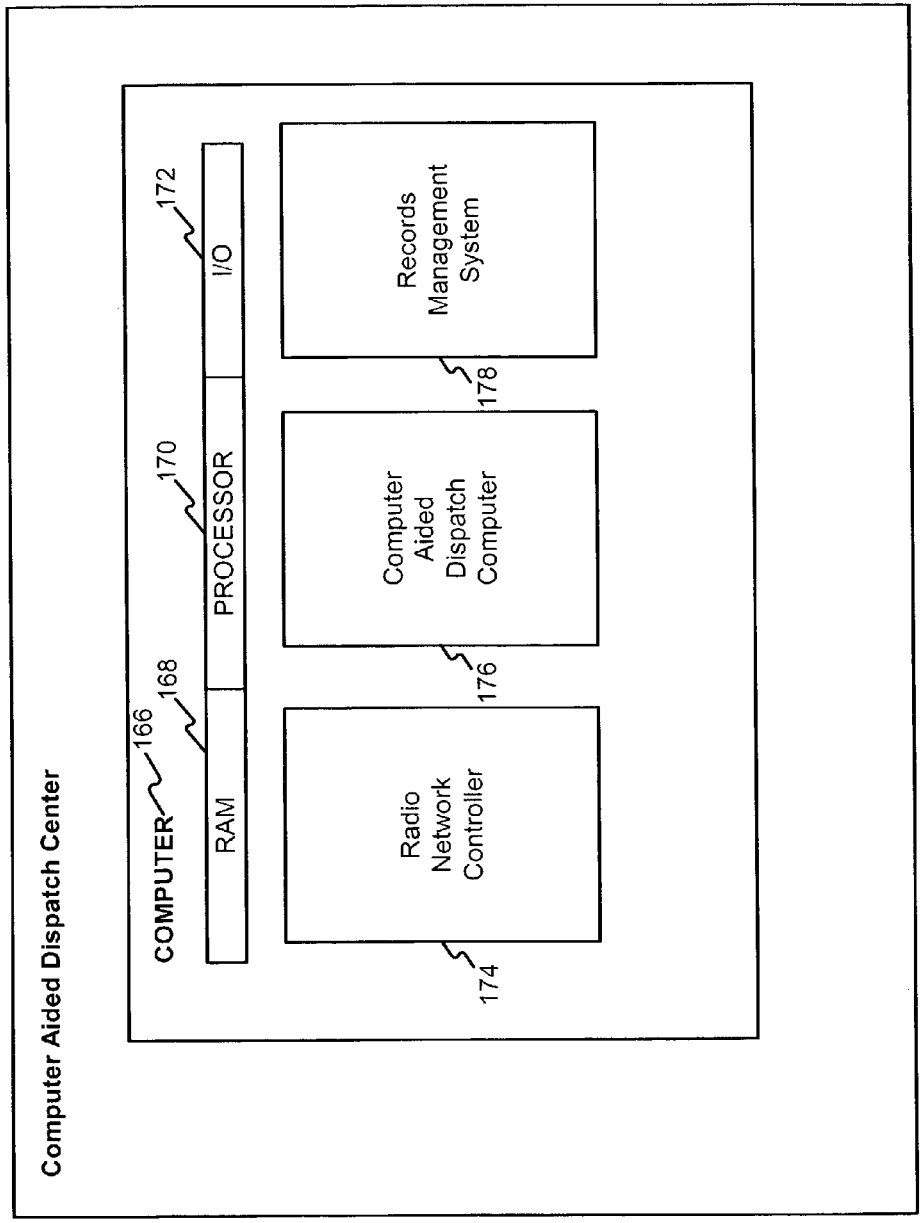
FIG. 1E is a schematic diagram illustrating an exemplary computer aided dispatch center consistent with the methods and systems of the present invention.

Referring now to FIG. 1E, an exemplary computer-aided dispatch center 164 is illustrated. Computer aided dispatch center (CAD) 164 may include a computer 166, a radio network controller (RNC) 174, a computer-aided dispatch computer (CAD) 176, and a records management system (RMS) 178. Computer 166 may further include a RAM 168, a processor 170, and an input/output I/O unit 172. In one embodiment, radio network controller 174 may interface with a radio frequency RF network, for example the Motorola RF network.

Figure 1F:
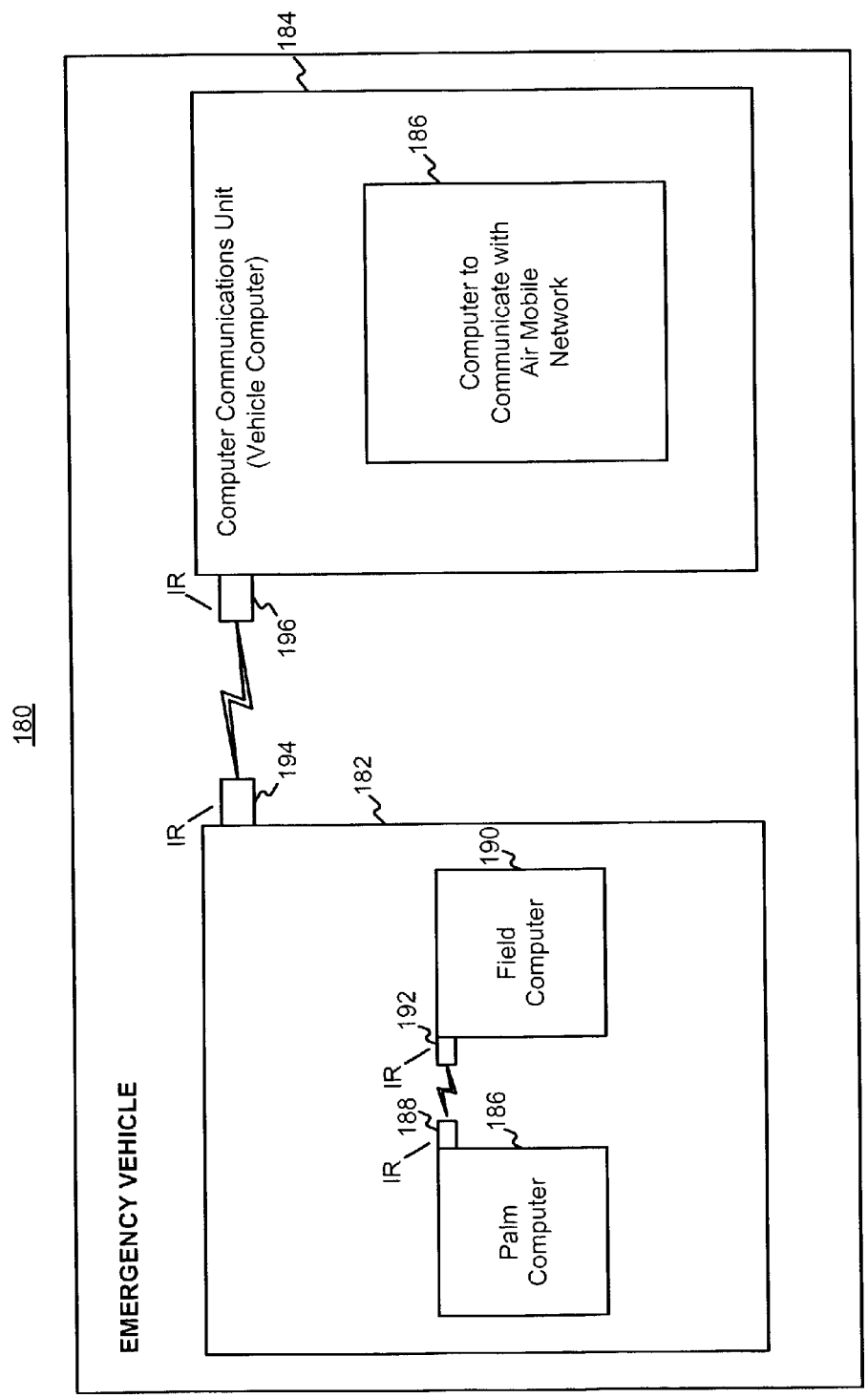
FIG. 1F is a schematic diagram illustrating exemplary computing modules in a vehicle consistent with the methods and systems of the present invention.

Referring now to FIG. 1F, an emergency vehicle 180 with a mobile computer 182 and a computer communications unit 184 is shown. In one embodiment, mobile computer 182 may be a palm computer. In one embodiment field computer may be a Hammer Head HH3 which may be obtained from Walkabout Computers, Inc. of Palm Beach, Fla. In one embodiment computer communications unit 184 may comprise a computer to communicate with air mobile network 186, which may be implemented using Motorola's MW250 with Custom Logic Design's ZClient Software.

Figure 2:
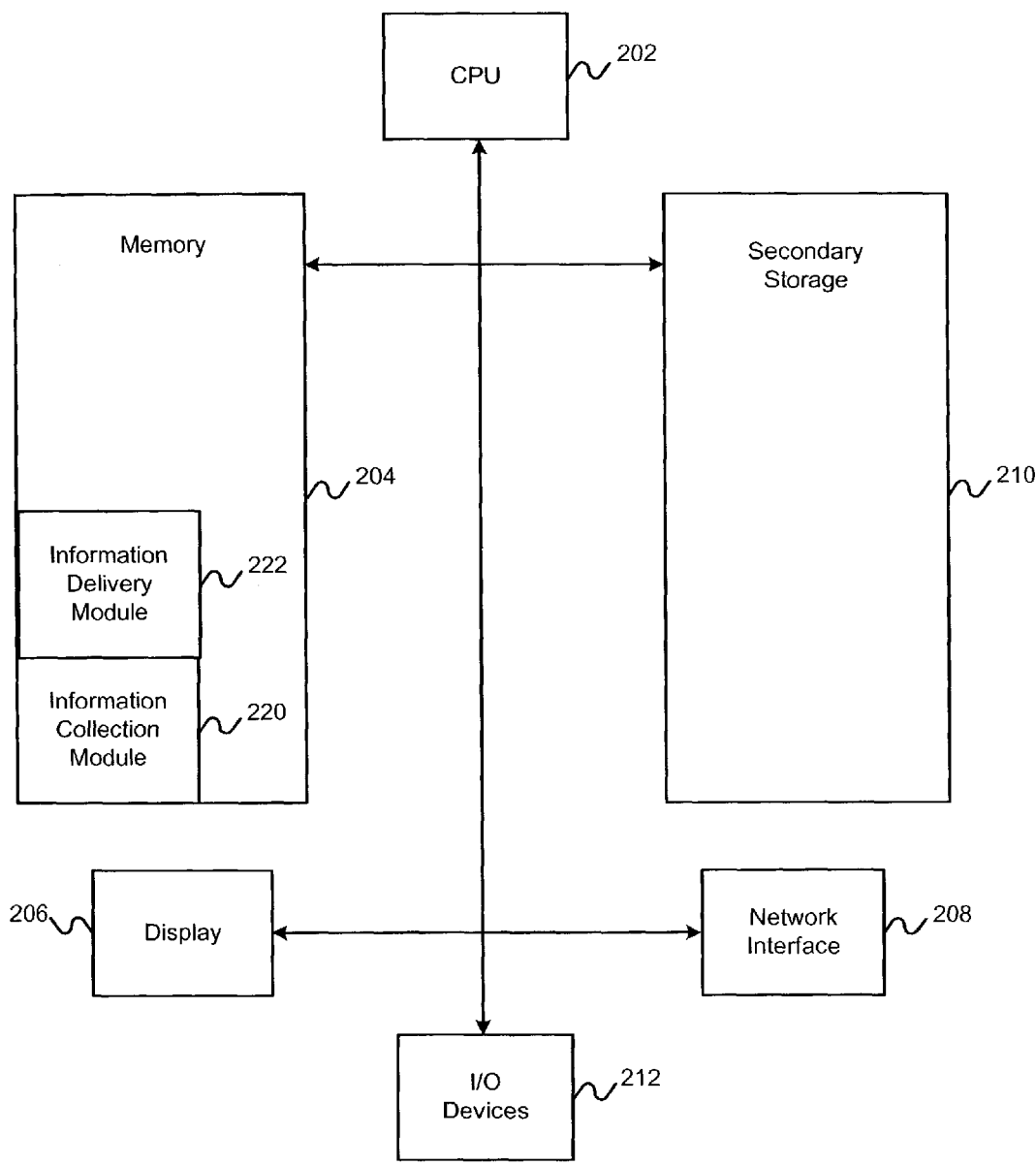
FIG. 2 is a schematic diagram illustrating an exemplary mobile computer consistent with the methods and systems of the present invention.

Referring now to FIG. 2, an exemplary mobile computer (such as 102 of FIG. 1A) is shown. The exemplary mobile computer 200 may comprise a CPU 202, a memory 204, a display 206, a network interface 208, a secondary storage 210, and I/O devices 212. Memory 204 may further include an information collection module 220 and an information delivery module 222. Information collection module 220 and information delivery module 222, when executed by CPU 202 (alone or in conjunction with other software not shown for example, an operating system), may provide the functionality associated with the mobile computer. Although FIG. 2 shows secondary storage 210 and I/O devices 212, respectively connected to the CPU, a mobile computer may not necessarily have these elements. Thus, for example, memory 204 may be a flash memory or some other type of memory that may serve as both memory for execution of programs and secondary storage memory. In one embodiment consistent with the present invention, mobile computer 200 may be a handheld computer such as a Compaq iPAQ, a palm computer, or any other handheld device providing the functionality associated with a hand-held computer.

Further, in one embodiment, information collection module 220 may be implemented using SafetyPAD-pocket software, which may be obtained from OPEN Incorporated of St. Paul, Minn. Alternatively, it may be implemented using SafetyPAD software (which may also be obtained from OPEN Incorporated of St. Paul, Minn.). Additionally, in one embodiment, information delivery module 222 may be implemented using iDelivery application also available from OPEN Incorporated of St. Paul, Minn.

Figure 3:
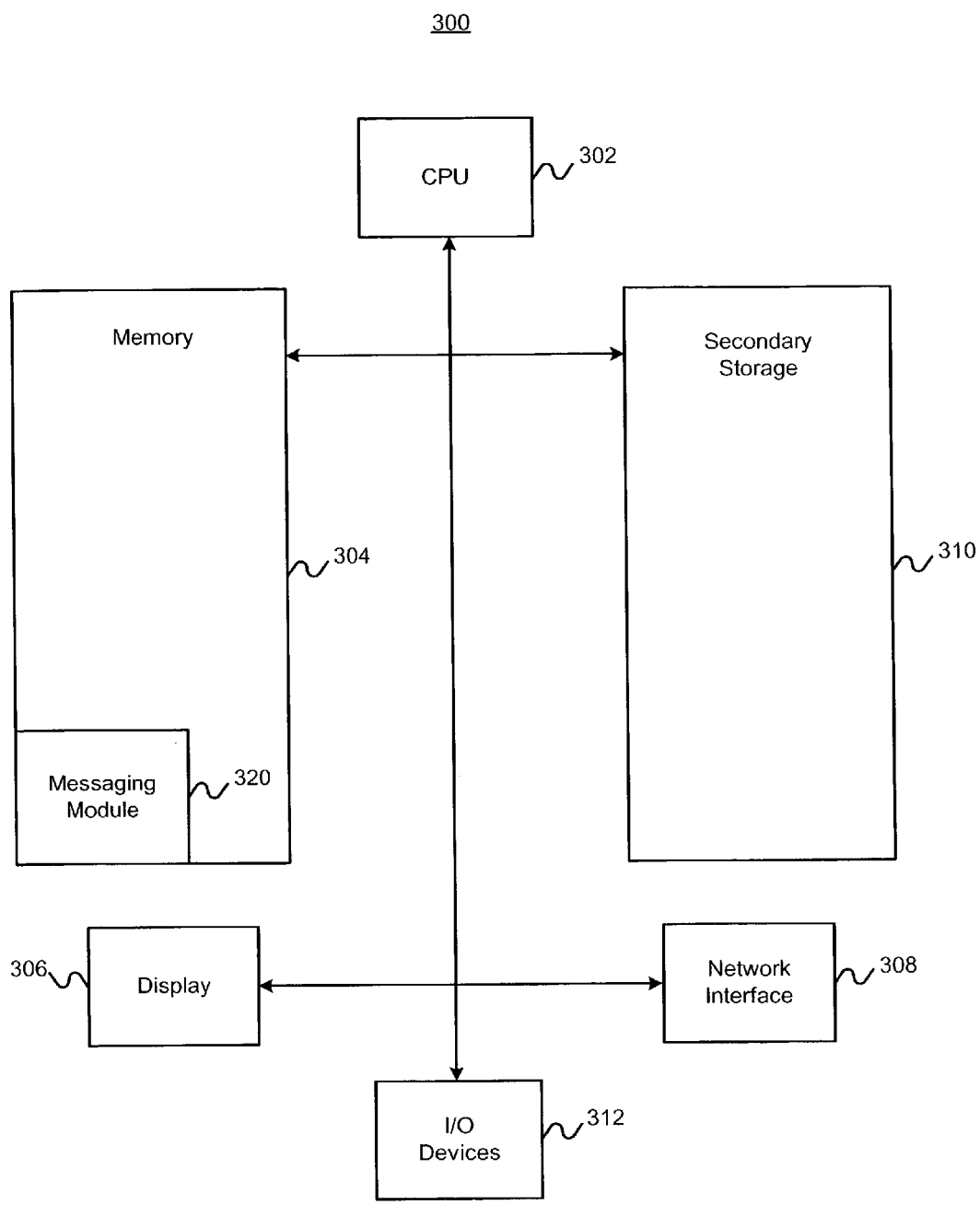
FIG. 3 is a schematic diagram illustrating an exemplary vehicle computer consistent with the methods and systems of the present invention.

FIG. 3 shows an exemplary vehicle computer 300 (such as 142 of FIG. 1C). Vehicle computer 300 may comprise a CPU 302, a memory 304, a display 306, a network interface 308, a secondary storage 310, and I/O devices 312. Memory 304 may further include a messaging module 320. Although not shown, vehicle computer 300 may further include an operating system and other software. In one embodiment, vehicle computer 300 may be implemented using Motorola's MW250 computer with Custom Logic Design's ZClient Software, which may implement messaging module 320. Also, as shown in FIG. 1F, mobile computer 200 (as shown in FIG. 2) may communicate with the vehicle computer 300 (as shown in FIG. 3) via a network interface or an IR port respectively. Although not shown in FIGS. 2 and 3, each of these computers may further have an infrared IR port to communicate with each other. Further, other types of technology such as Bluetooth, IEEE 802.11, or any other communication protocol or standard may be used to establish a communication link between the mobile computer and vehicle computer.

FIG. 4 shows an exemplary electronic file 400 corresponding to medical information for transmission from a mobile computer to a medical facility. As shown, electronic file 400 may include information including patient name, present history, past history, care events, and findings. Of course, alternative or additional information may be included.

Figure 5:
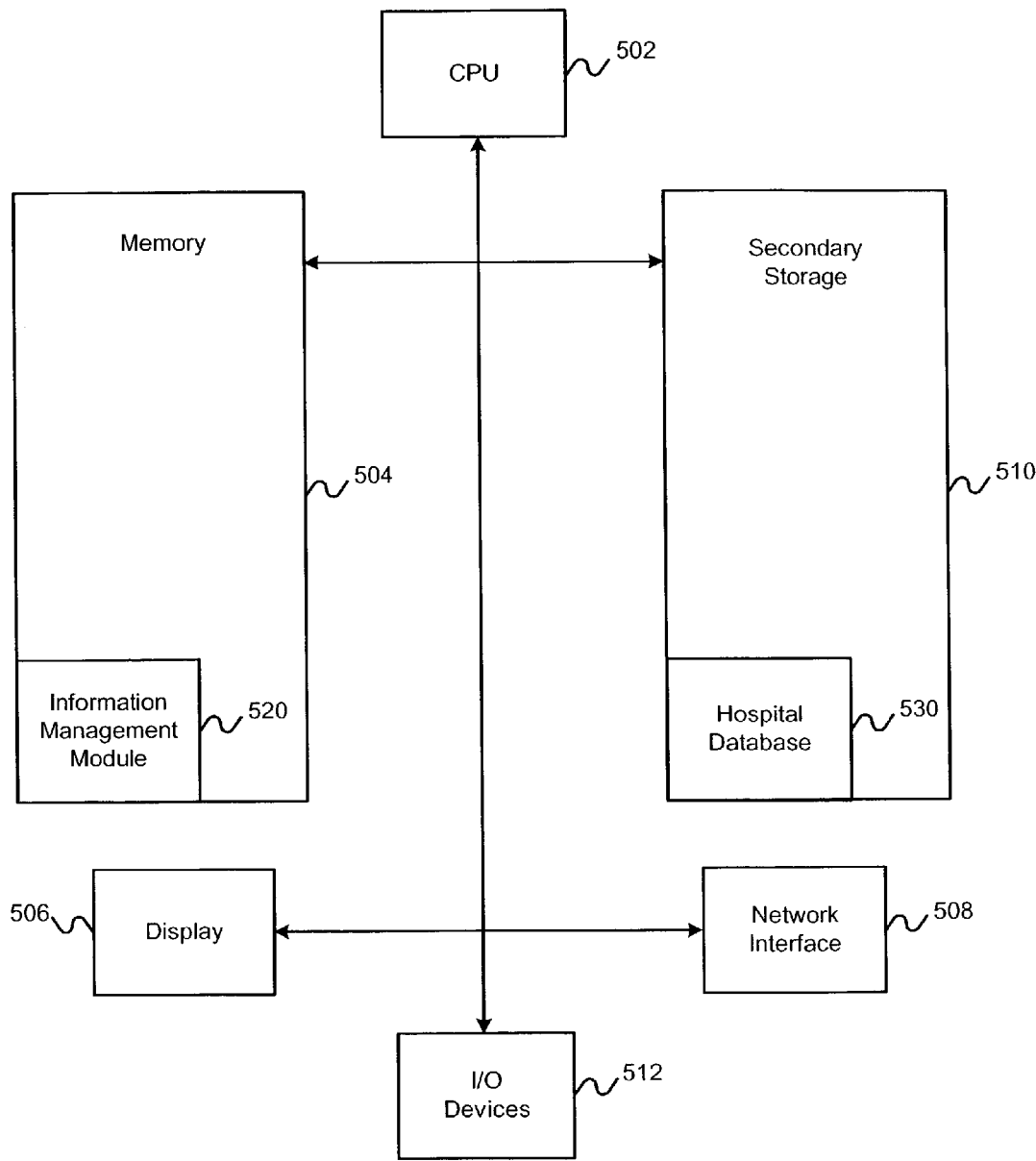
FIG. 5 is a schematic diagram illustrating an exemplary hospital computer consistent with the methods and systems of the present invention.

FIG. 5 shows an exemplary computer located at a medical facility. The exemplary medical facility computer 500 may include a CPU 502, a memory 504, a display 506, a network interface 508, a secondary storage 510 and I/O devices 512. Memory 504 may further include an information management module 520. Further, although not shown, memory 504 may include other components or modules to enable the CPU 502 to execute the functionality associated with the medical facility computer 500. Secondary storage 510 may further include a hospital database 530. Hospital database 530 may be a distributed database such that other components of hospital database 530 may reside on other computers.

Further 6A depicts an exemplary bill processing computer 600. Bill processing center computer 600 may include a CPU 602, a memory 604, a display 606, a network interface 608, a secondary storage 610, and I/O devices 612. Memory 604 may further include a bill processing module 620 and a notification module 622. Bill processing module 620 and notification module 622, when executed alone or in conjunction with other software not shown by the CPU 602, may provide the functionality associated with the bill processing center computer. Secondary storage 610 may further include a billing database 630. Billing database 630 may be a centralized database or alternatively it may be a distributed database.

Figure 6A:
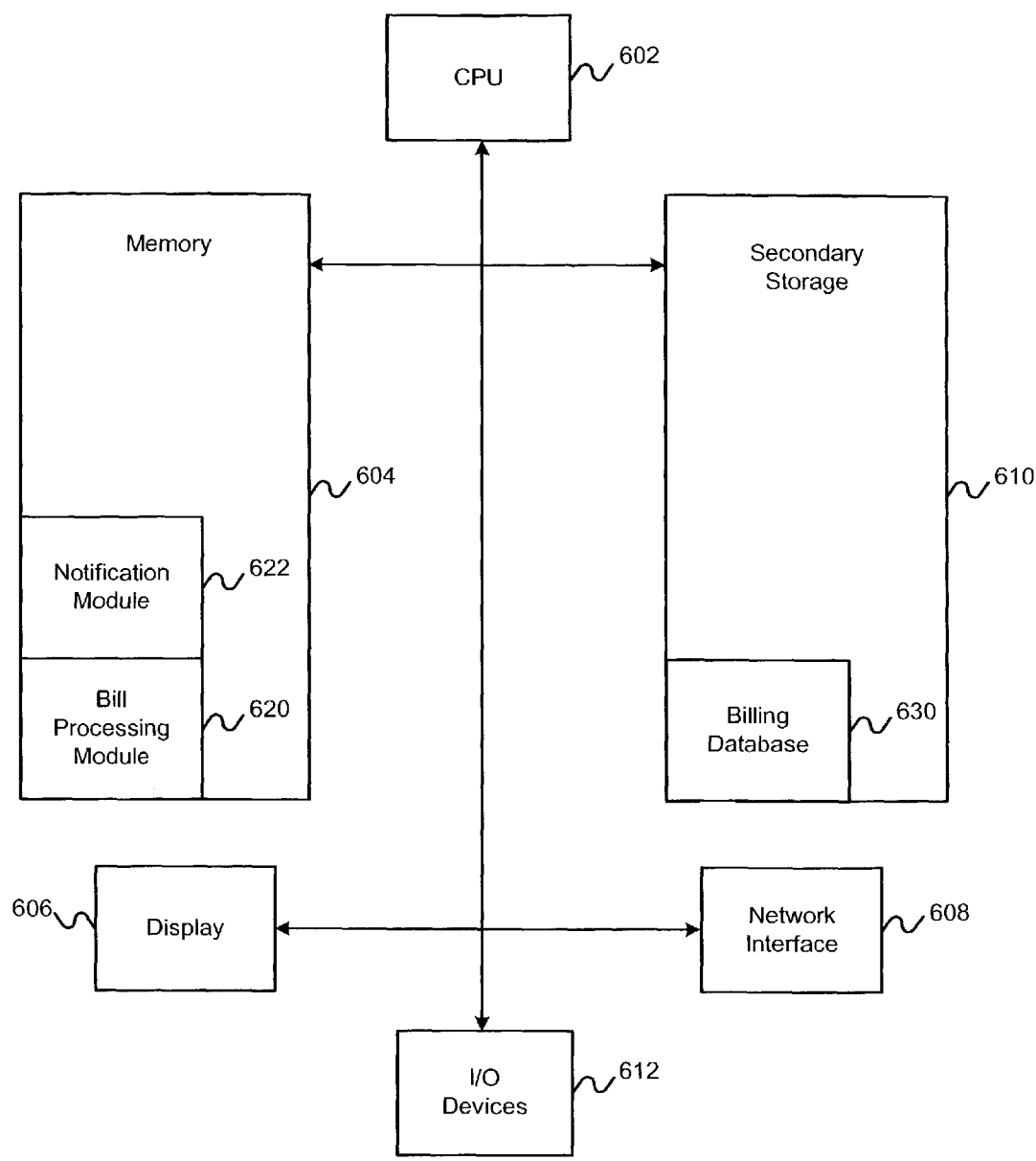
FIG. 6A is a schematic diagram illustrating an exemplary bill processing center computer consistent with the methods and systems of the present invention.
Figure 6B:
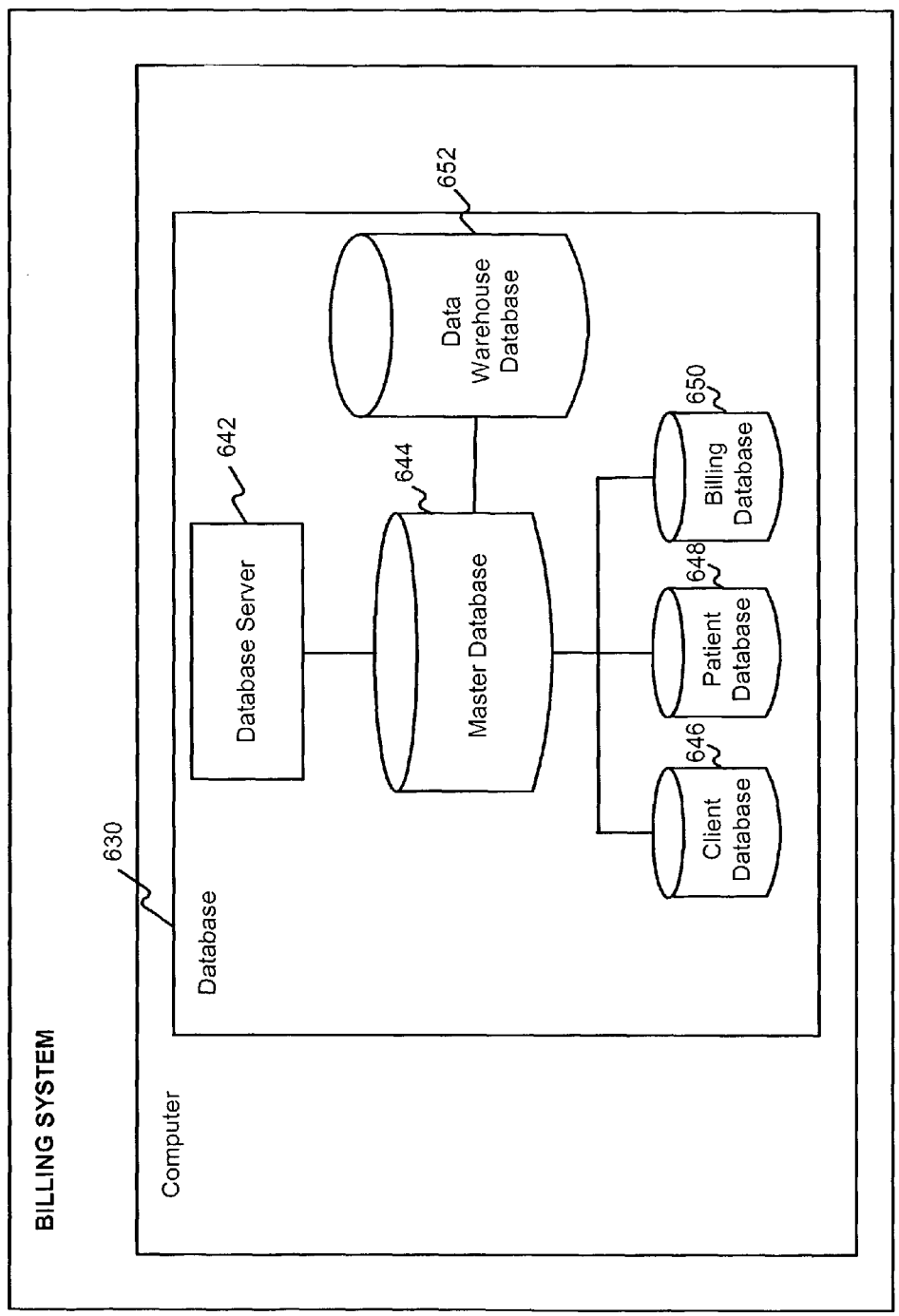
FIG. 6B is a schematic diagram illustrating an exemplary billing system database consistent with the methods and systems of the present invention.

FIG. 6B is a schematic diagram illustrating an exemplary billing system 630, which may be located at the bill processing center. Billing system 630 may include a database server 642, a master database 644, a client database 646, a patient database 648, and a billing database 650. Billing system 630 may further include a data warehouse database 652. Data warehouse database 652 may act as a backup database to the database 630. Each of these databases may be located on the same computer or may be distributed. Master database 644 may be used to maintain information from all of the other databases together. Client database 646 may have tables and information related only to clients, for example, purchasers of medical/emergency medical services. Patient database 648 and billing database 650 are discussed further with respect to FIGS. 7 and 8 respectively.

Figure 6C:
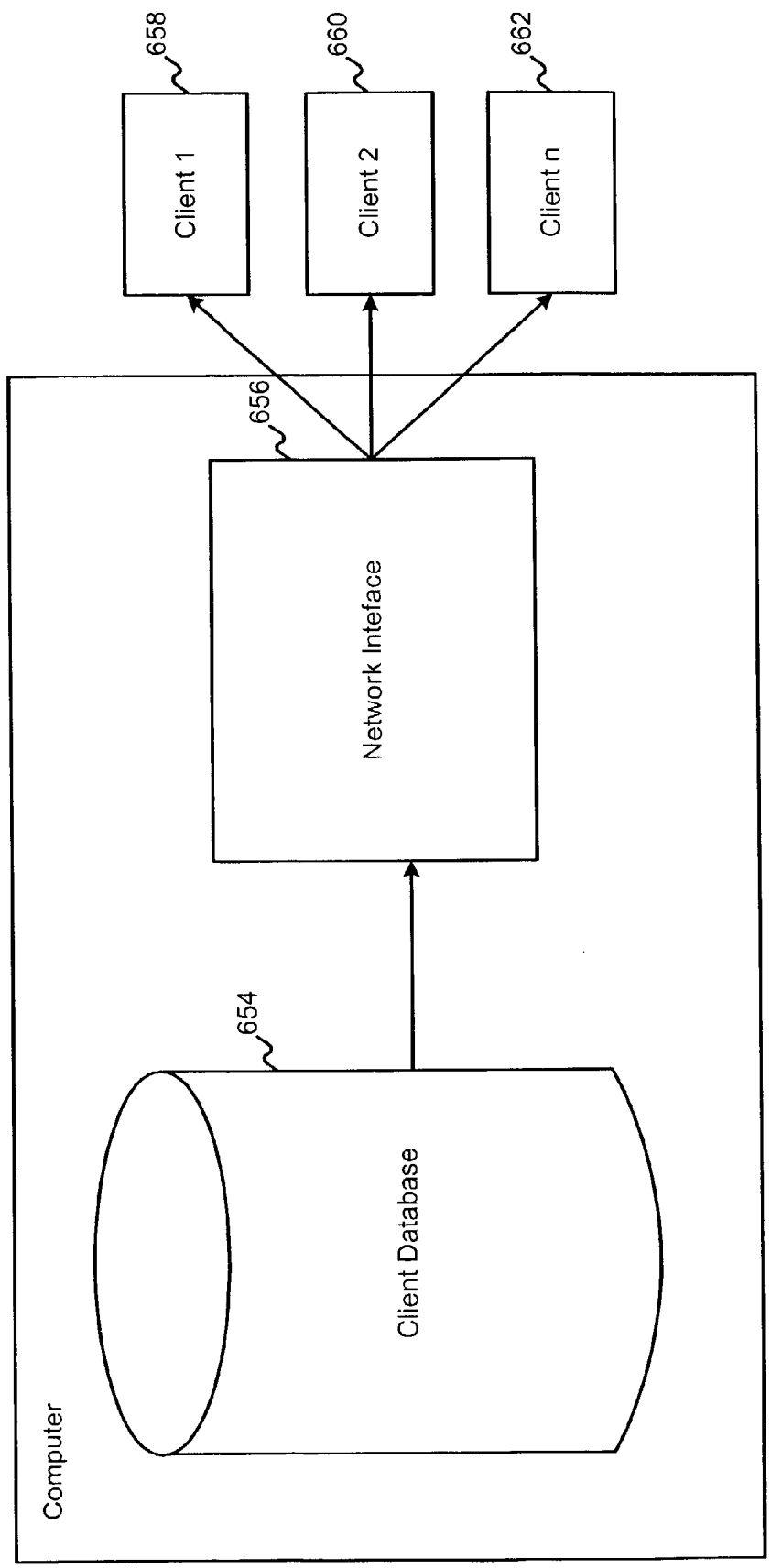
FIG. 6C is a schematic diagram illustrating an exemplary system environment for a client database consistent with methods and systems of the present invention.

FIG. 6C is a schematic diagram illustrating an exemplary system environment for a client database 654 (such as 646 of FIG. 6B). Client database 654 may be connected via a network interface 656 to client 1 658, client 2 660, and client n 662, permitting each of these clients to access data located on the client database 653. By accessing the client database, the clients may access client reports, for example.

Figure 6D:
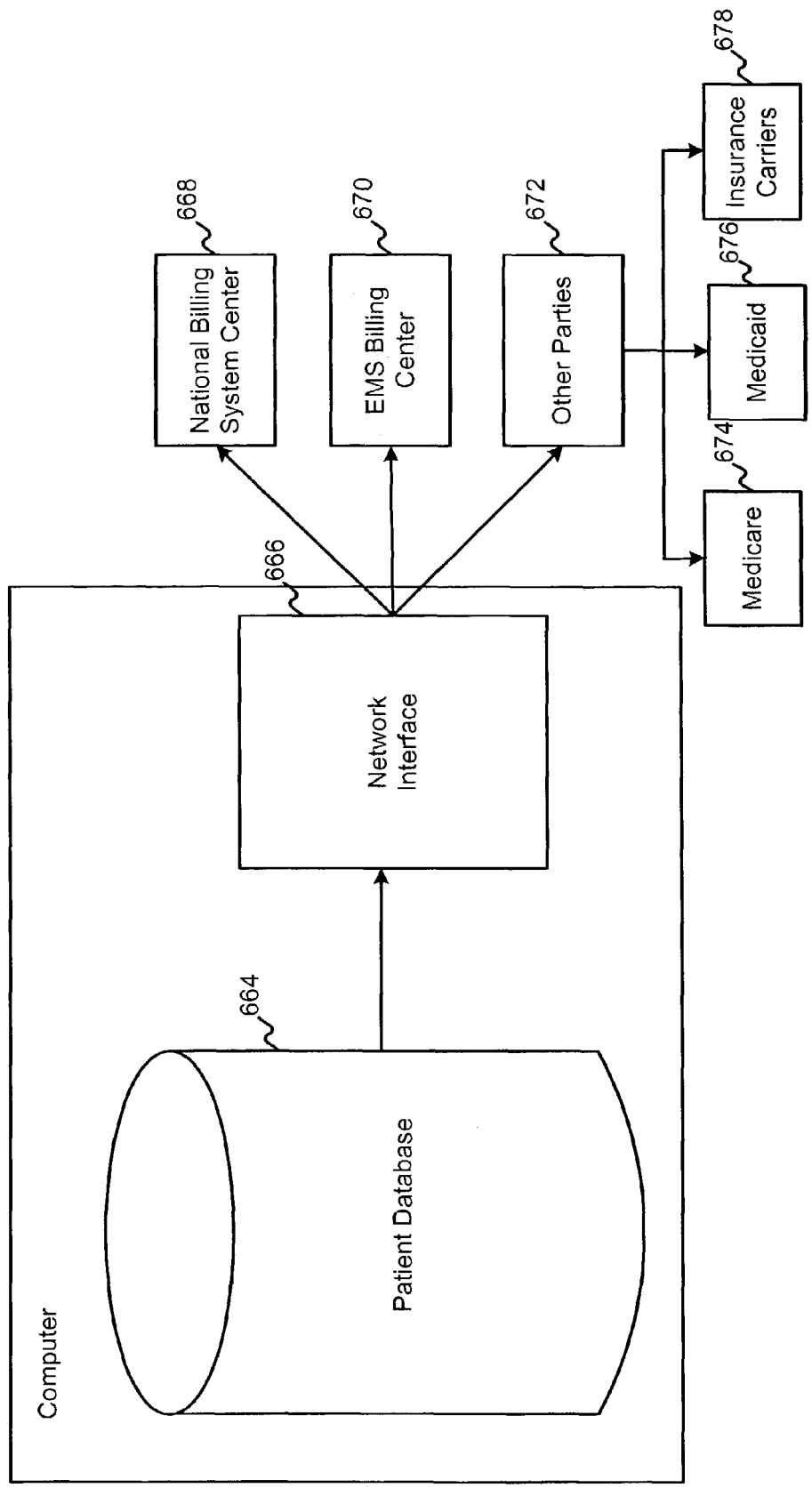
FIG. 6D is a schematic diagram illustrating an exemplary system environment for a patient database consistent with the methods and systems of the present invention.

FIG. 6D is a schematic diagram illustrating an exemplary system environment for a patient database 664 (such as 648 of FIG. 6B). Patient database 664 may be connected via a network interface 666 to a national billing system center 668, an EMS billing center 670, and other parties 672. It may also be connected either directly or via the other parties (as shown in FIG. 6D) to payors, such as Medicare 674, Medicaid 676, and insurance carriers 678.

Figure 6E:
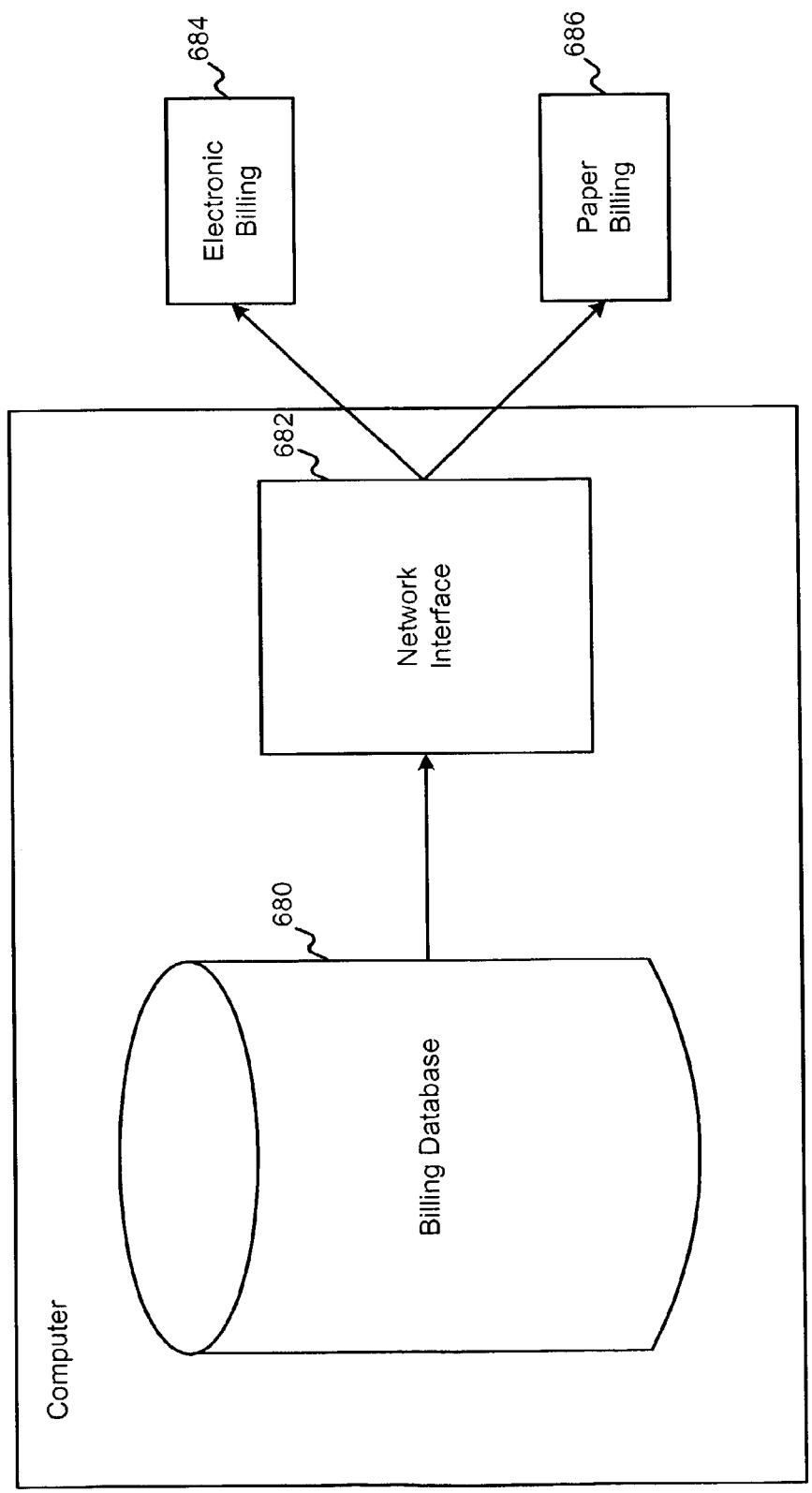
FIG. 6E is a schematic diagram illustrating an exemplary system environment for a billing database consistent with the methods and systems of the present invention.

FIG. 6E is a schematic diagram illustrating an exemplary system environment for a billing database 680 (such as 650 of FIG. 6B). Billing database 680 may be connected via a network interface 682 to an electronic billing module 684 and a paper billing module 686. Using electronic billing module 684 bills may be generated automatically. Additionally, a bill may be sent electronically to a patient, for example. Alternatively, a paper bill may be generated (automatically or manually) using paper billing module 686 and may then be sent to the patient.

Figure 6F:
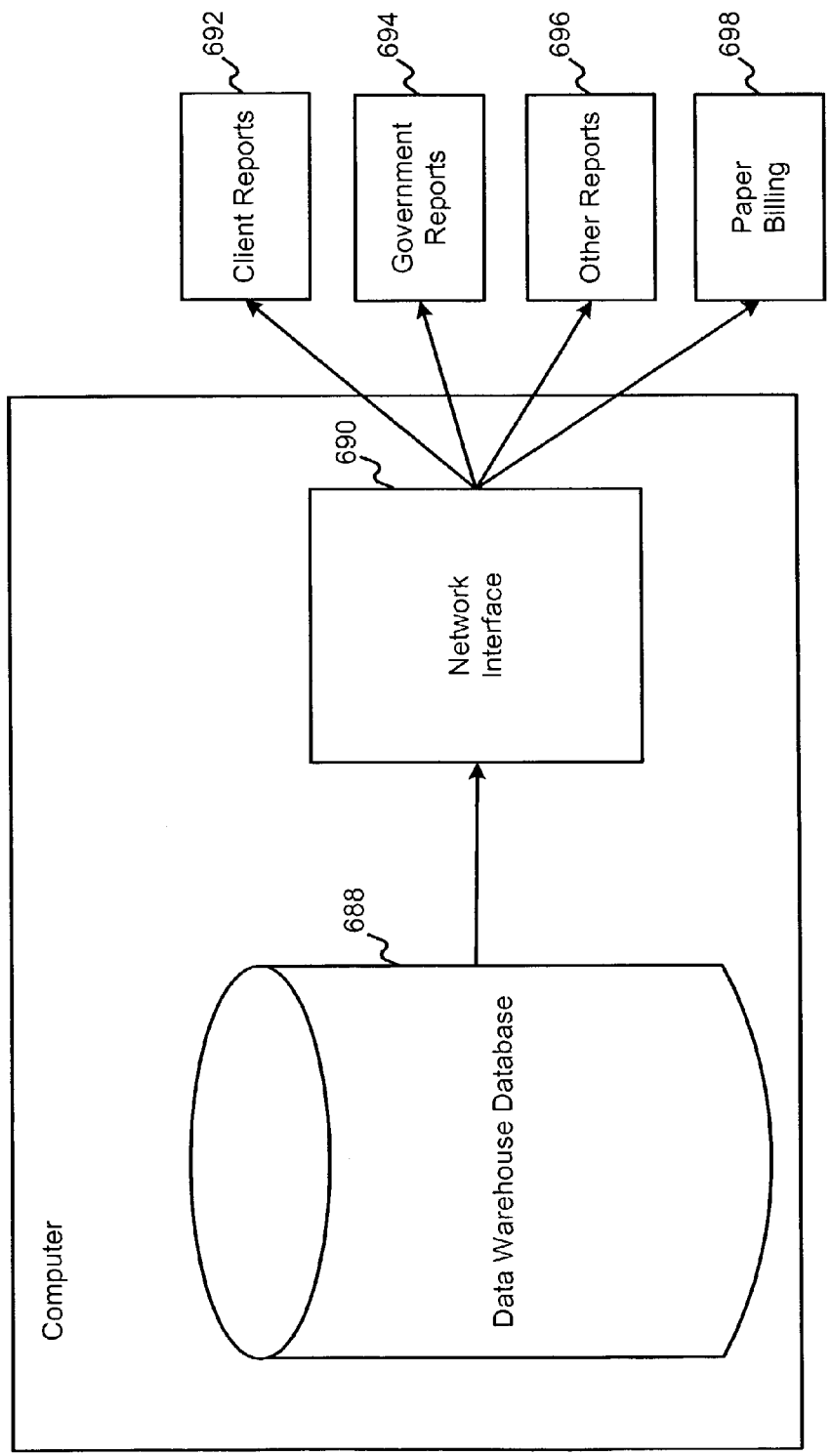
FIG. 6F is a schematic diagram illustrating an exemplary system environment for a data warehouse database consistent with the methods and systems of the present invention.

FIG. 6F is a schematic diagram illustrating an exemplary system environment for a data warehouse database 688. Data warehouse database 688 may be connected via a network 690 to a client reports module 692, a government reports 694 module, other reports module 696, and a paper billing module 698.

FIG. 7 is a schematic diagram illustrating exemplary information stored in a patient database (such as patient database 664 of FIG. 6D). As shown, this information may include medical and related information. Thus, for example, it may include a patient id 710, a corresponding patient name 720, a present Hx (history) 730, a past Hx (730), findings 750, a patient address 760, and a type of insurance coverage available to the patient 780. Present Hx 730 may relate to the present condition(s) of a patient, such as abdominal pain, dizziness, head trauma, and/or bleeding arm. Past Hx 730 may relate to past condition(s), including existing conditions, allergies, and/or information regarding past hospital stays. Findings 750 may relate to any observations related to the patient's condition, such as whether the patient was alert or unconscious. Type of coverage 780 may relate to the type of at least one coverage that the patient may have, including, for example, coverage through private medical insurance, Medicare, Medicaid, and/or self-pay. Although FIG. 7 shows only one table with a limited number of columns and corresponding rows, the patient database may contain several such tables, which may have additional columns and rows. For example, a column labeled "code" may include information concerning a code into which a medical service may be classified. Moreover, the patient database may be a distributed database, a relational database, and/or any other type of database capable of storing patient related information.

FIG. 8 is a schematic diagram illustrating exemplary information stored in a billing database (such as 680 of FIG. 6E). As shown, the exemplary information stored in the billing database may include a patient id 810, a corresponding patient name 820, a patient address 830, a service rendered 840, a name of physician 850, a bill status 860, a payment status 870, a type of coverage 880, and a code 890 (such as a billing code corresponding to a billing category). Service rendered 840 may include any service(s) rendered by paramedics, for example, at an emergency vehicle, including transportation to a hospital. Bill status 860 may relate to the processing status of a bill, such as whether the bill has been sent or is being processed. Payment status 870 may include information regarding whether a bill has been paid or not. Type of coverage 880 may include the same information as the patient database discussed above. Code 892 may relate to, for example, a billing category. Although FIG. 8 shows only a limited number of columns and corresponding rows, the billing database may contain several such tables, which may have additional columns and rows. Moreover, the billing database may be a distributed database, a relational database, and/or any other type of database capable of storing billing related information.

Figure 9:
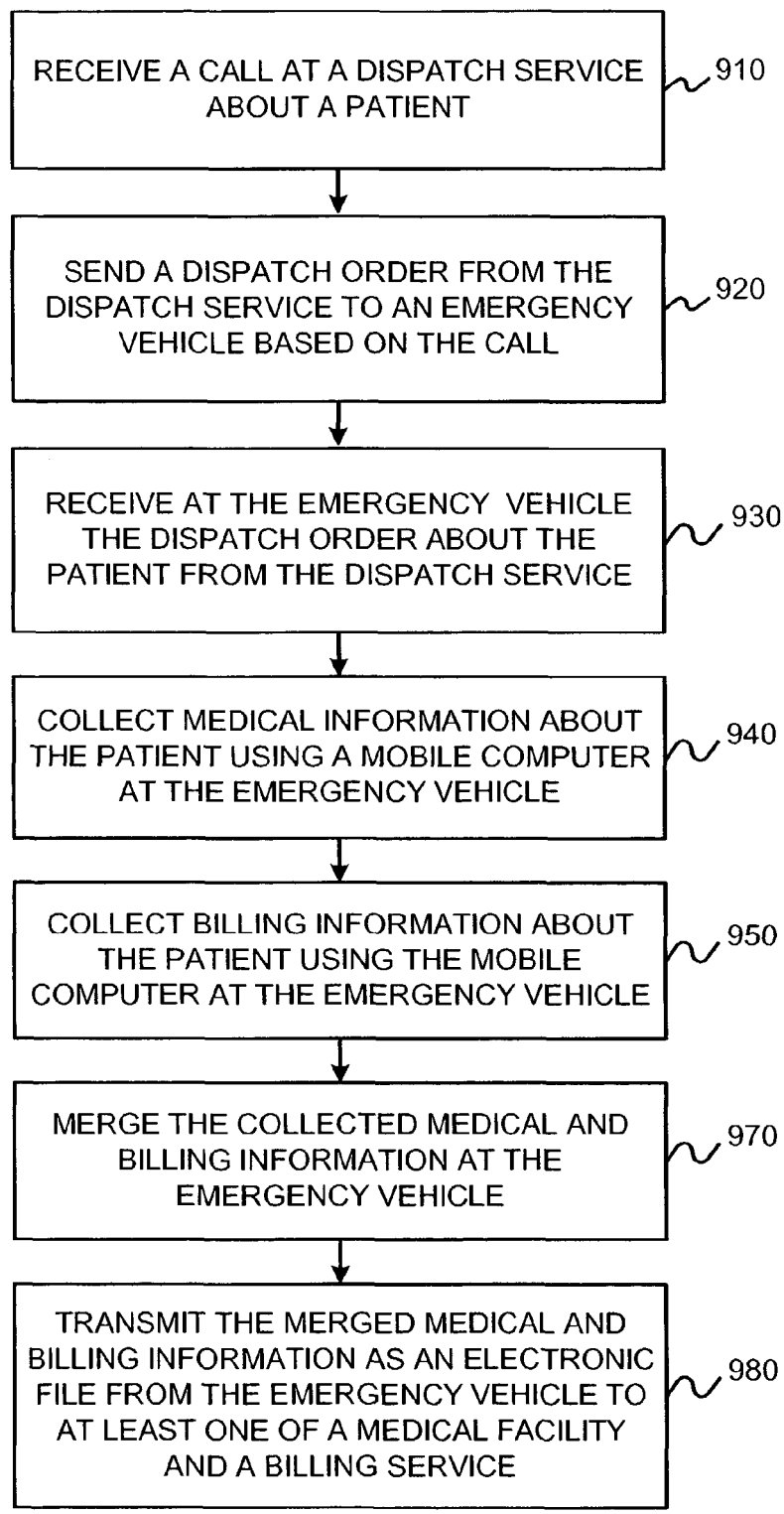
FIG. 9 is a flow diagram illustrating an exemplary method for collecting medical and billing information about a patient at an emergency vehicle consistent with the methods and systems of the present invention.

FIG. 9 is a flow diagram illustrating an exemplary method for collecting medical and billing information about a patient at an emergency vehicle. The exemplary method may involve receiving a call at a dispatch service about the patient (step 910). This call may be received, for example, at a computer-aided dispatch center 164 (FIG. 1E).

The method may further include sending a dispatch order from the dispatch service to the emergency vehicle based on the call (step 920). The dispatch order may be sent via, for example, the radio network controller 174 of FIG. 1E. Of course, other communication means may also be used to send the dispatch order from the dispatch service to the emergency vehicle.

Next, the method may include receiving at the emergency vehicle the dispatch order about the patient from the dispatch service (step 930). The dispatch order may be received by vehicle computer 184 at emergency vehicle 180 of FIG. 1F, for example.

Further, the method may include collecting medical information about the patient using mobile computer (for example 186 of FIG. 1F) at the emergency vehicle (step 950). In one embodiment, the medical information about the patient may be collected using mobile computer 200 (an example of which is depicted in more detail in FIG. 2). Further, an information collection module 220, alone or in conjunction with other modules/software, may be used to collect the medical information.

Moreover, the method may further include collecting billing information about the patient using the mobile computer at the emergency vehicle (step 950). In one embodiment, the billing information about the patient may be collected using the mobile computer depicted in FIG. 2. Further, an information collection module 220, alone or in conjunction with other modules/software, may be used to collect the billing information. Of course, the functionality associated with the information collection module may be further distributed into sub-modules and/or combined with other modules.

Next, the collected medical and billing information may be merged at the emergency vehicle (step 970). In one embodiment, information collection module 220 may be used to merge the collected medical and billing information.

Further, the merged medical and billing information may be transmitted as an electronic file from the emergency vehicle to at least one of a medical facility and a billing service (step 980). Alternatively, the merged medical and billing information may be transmitted to a vehicle computer (such as shown in FIGS. 1C and 3) (step 1010 of FIG. 10). The vehicle computer may receive the merged medical and billing information from the information delivery module of the mobile computer through, for example, an infrared (IR) port. As noted earlier, any other appropriate technology, such as Bluetooth may also be used to receive the merged medical and billing information. The vehicle computer may then transmit the merged medical and billing information to a medical facility over a network (step 1020 of FIG. 10). The network used may be a Motorola RF network. Additionally and/or alternatively, the vehicle computer may transmit the merged medical and billing information to a medical facility over a redundant network. The redundant network used may be a wide-area network.

Figure 10:
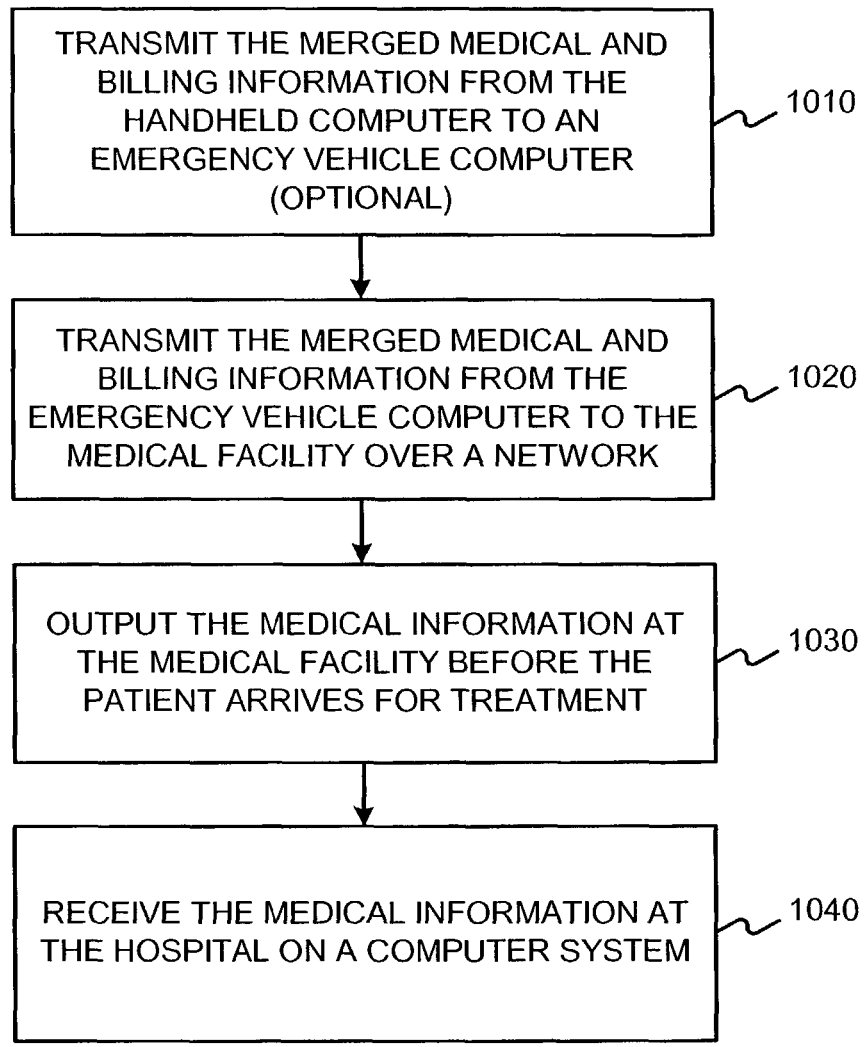
FIG. 10 is a flow diagram illustrating an exemplary method for collecting information about a patient at a vehicle consistent with the methods and systems of the present invention.

Referring further to FIG. 10, the medical information may be output at a medical facility before the patient arrives for treatment (step 1030). The medical facility, may include, for example, a hospital. Further, the medical information may be received at the hospital on a computer system (step 1040). An exemplary computer system at the hospital (for example, as shown in FIG. 5 and FIG. 1C (148)) may include at least one of a computer, a network interface, an IR port, and a printer.

Although not shown in FIGS. 9 and 10, the exemplary method may further include outputting the billing information at a billing service for automatic billing. The automatic billing may be at least for the dispatch order. Thus, for example, this way a patient may be billed automatically for any services rendered to the patient, including transportation to a medical facility.

Figure 11:
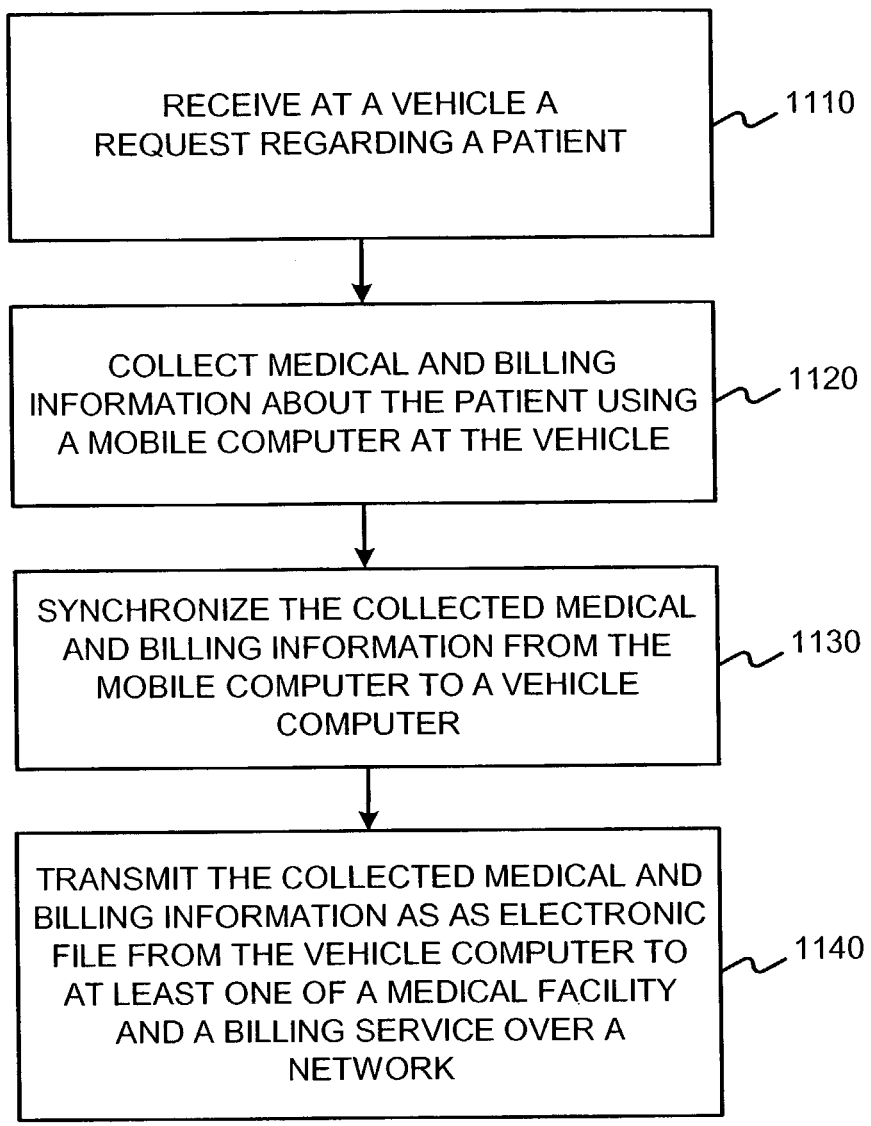
FIG. 11 is a flow diagram illustrating another exemplary method for collecting information about a patient at a vehicle consistent with the methods and systems of the present invention.

FIG. 11 is a flow diagram illustrating another exemplary method for collecting information about a patient at a vehicle. This method may include receiving at a vehicle a request regarding a patient (step 1110). In one embodiment, the request may be received from a dispatch center.

Next, the method may include collecting medical and billing information about the patient using a mobile computer at the vehicle (step 1120). In one embodiment, the medical and billing information about the patient may be collected using the mobile computer depicted in FIG. 2. Further, an information collection module 220, alone or in conjunction with other modules/software, may be used to collect the medical and billing information. Of course, the functionality associated with the information collection module may be further distributed into sub-modules and/or combined with other modules. Also, the mobile computer may be a handheld computer, a palm computer, and/or a field computer.

Next, the method may include synchronizing the collected medical and billing information from the mobile computer to a vehicle computer (step 1130). Synchronization may be achieved using, for example, information collection module 220, alone or in conjunction with other modules/software.

Further, the method may include transmitting the collected medical and billing information as an electronic file from the vehicle computer to at least one of medical facility and a billing service over a network (step 1140). In one embodiment, the network may be a Motorola RF network. Alternatively and/or additionally, the collected medical and billing information may be transmitted as an electronic file from the vehicle computer to at least one of medical facility and a billing service over a redundant network, such as a wide-area network. The medical information may be output at a medical facility before the patient arrives for treatment. The medical facility, may include, for example, a hospital. Further, the medical information may be received at the hospital on a computer system. An exemplary computer system at the hospital (for example, as shown in FIG. 5 and FIG. 1C (148)) may include at least one of a computer, a network interface, an IR port, and a printer.

Although not shown in FIG. 11, the exemplary method may further include outputting the billing information at the billing service for automatic billing. The automatic billing may be at least for the dispatch order.

Figure 12:
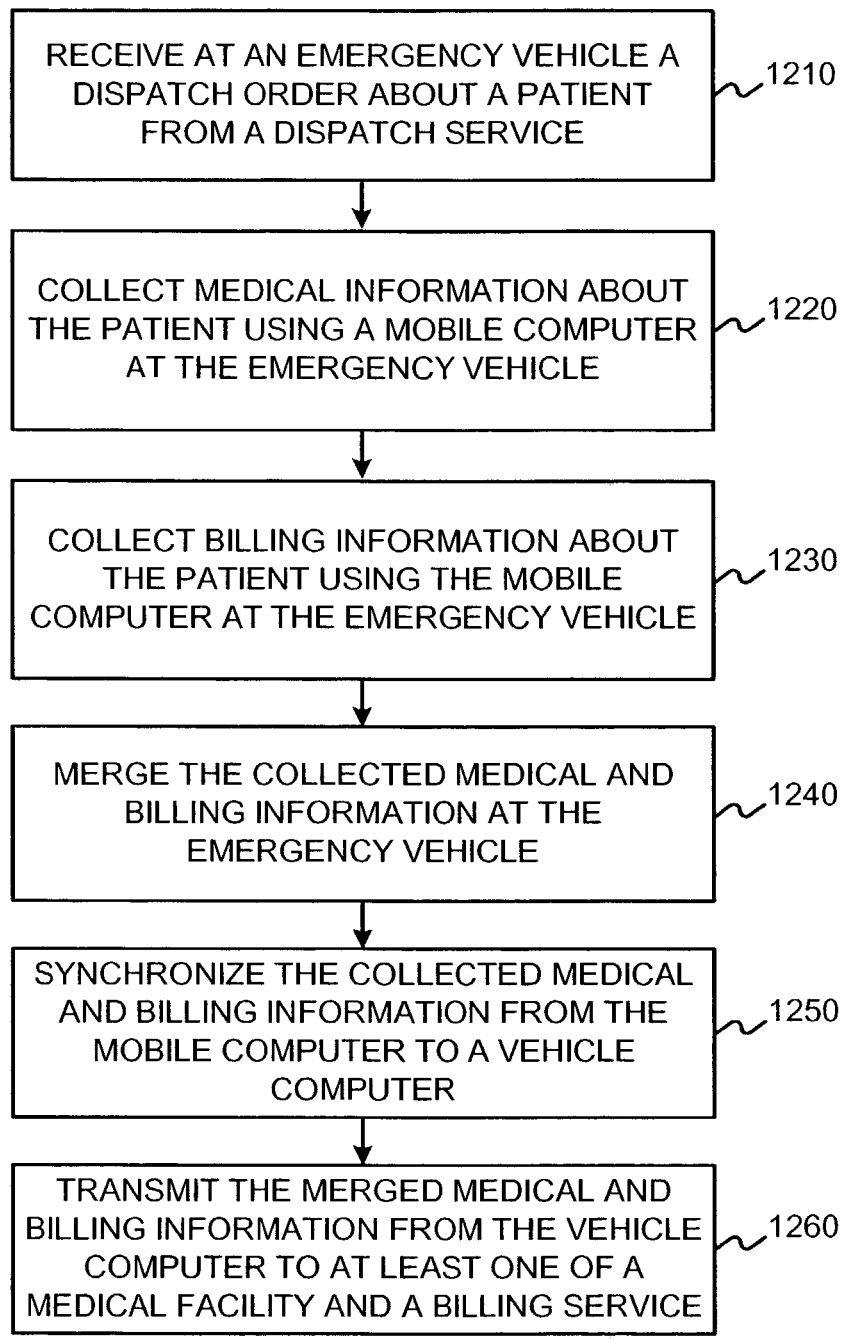
FIG. 12 is a flow diagram illustrating an exemplary method for collecting medical and billing information about a patient at an emergency vehicle consistent with the methods and systems of the present invention.

FIG. 12 is a flow diagram illustrating an exemplary method for collecting medical and billing information about a patient at an emergency vehicle. As shown, the exemplary method may include receiving at the emergency vehicle a dispatch order about the patient from a dispatch service (step 1210). The dispatch order may be received via a vehicle computer, which may have been sent from the radio network controller of FIG. 1E. Indeed, any other communication means may be used to receive the dispatch order.

Next, the method may include collecting medical information about the patient using a mobile computer at the emergency vehicle (step 1220).

Further, the method may include collecting billing information about the patient using the mobile computer at the emergency vehicle (step 1230). In one embodiment, the medical and billing information about the patient may be collected using the mobile computer depicted in FIG. 2. The mobile computer may be a handheld computer, a palm computer, a field computer (such as a HH3). Further, an information collection module 220, alone or in conjunction with other modules/software, may be used to collect the medical and billing information.

Next, the method may include merging the collected medical and billing information at the emergency vehicle (step 1240). Moreover, the method may include synchronizing the collected medical and billing information from the mobile computer to a vehicle computer (step 1250).

Next, the method may include transmitting the merged medical and billing information as an electronic file from the vehicle computer to at least one of a medical facility and a billing service (step 1260). Although not shown in FIG. 12, the exemplary method may further include additional steps as discussed above with respect to FIGS. 10 and 11.

Figure 13:
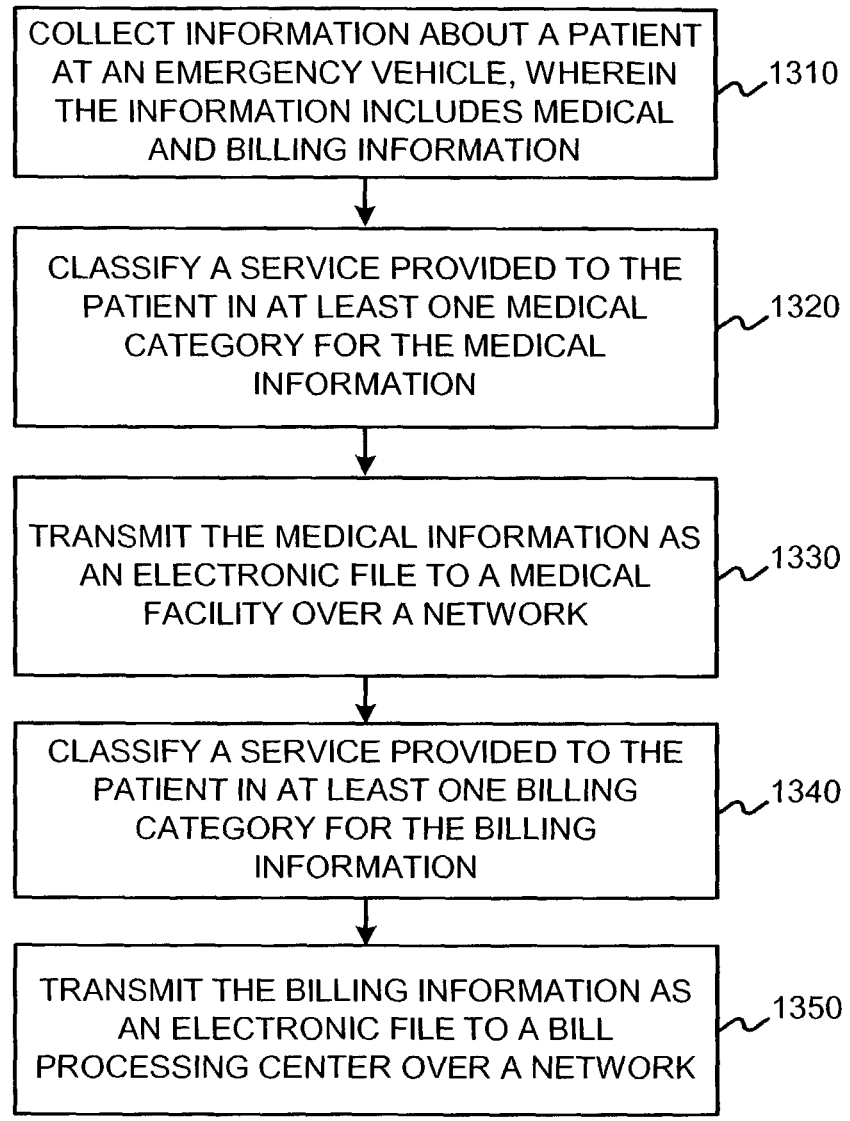
FIG. 13 is a flow diagram illustrating an exemplary method for processing medical and billing information about a patient at an emergency vehicle consistent with the methods and systems of the present invention.

FIG. 13 is a flow diagram illustrating an exemplary method for processing medical and billing information about a patient at an emergency vehicle. The exemplary method may include collecting information about the patient at the emergency vehicle, wherein the information includes medical and billing information (step 1310). In one embodiment, the medical and billing information about the patient may be collected using the mobile computer depicted in FIG. 2. The mobile computer may be a handheld computer, a palm computer, a field computer (such as a HH3). Further, an information collection module 220, alone or in conjunction with other modules/software, may be used to collect the medical and billing information.

Next, the method may include classifying a service provided to the patient in at least one medical category for the medical information (step 1320). The medical information may include at least one of a patient identification, a patient name, a present history, a past history, findings, and a patient address.

Moreover, the method may include transmitting the medical information as an electronic file to a medical facility (which may be a hospital) over a network (step 1330).

Further, the method may include classifying a service provided to the patient in at least one billing category for the billing information (step 1340). The billing information may include at least one of a patient identification, a patient name, a patient address, and a billing code.

Next, the method may include transmitting the billing information as an electronic file to a bill processing center over a network (step 1350). Although not shown in FIG. 13, the method may further include sending a first notice to the patient to collect additional information concerning the patient. Such additional information may include information concerning the type of health coverage the patient has, including, for example, Medicare, Medicaid, or health insurance. Additionally, the patient may pay out of his/her pocket for the healthcare expenses. The exemplary method may further include sending a second notice to the patient based on the response to the first notice.

Further, the exemplary method may include generating at least one of a client report, a government report, and other report based on the billing information. Such reports may be generated using data from any of the databases, such as the patient database, the client database, and the billing database (see, for example FIG. 6B).

Additionally, the method may further include obtaining type of health coverage information for the patient at the emergency vehicle and verifying health coverage information for the patient at the emergency vehicle.

Figure 14:
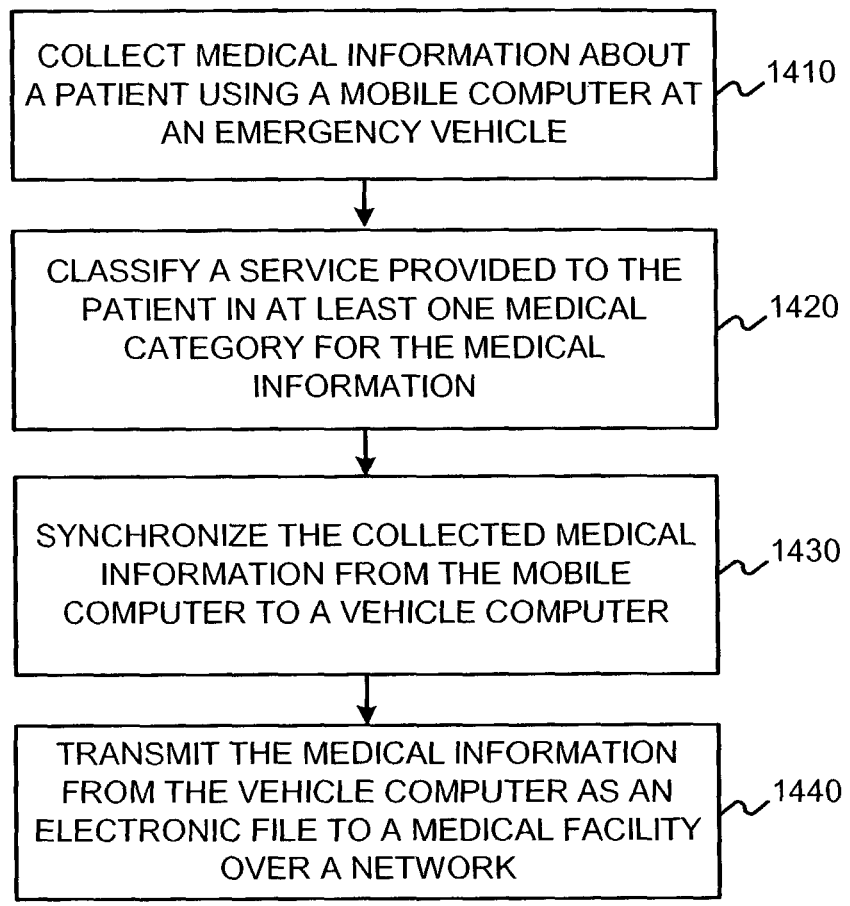
FIG. 14 is a flow diagram illustrating an exemplary method for processing medical information about a patient at an emergency vehicle consistent with the methods and systems of the present invention.

FIG. 14 is a flow diagram illustrating an exemplary method for processing medical information about a patient at an emergency vehicle. The exemplary method may include collecting medical information about the patient using a mobile computer at the emergency vehicle (step 1410). The medical information may include at least one of a patient identification, a patient name, a present history, a past history, a finding, and a patient address.

The method may further include classifying a service provided to the patient in at least one medical category for the medical information (step 1420). The method may also include synchronizing the collected medical information from the mobile computer to a vehicle computer (step 1430). The medical information may then be transmitted from the vehicle computer as an electronic file to a medical facility over a network. Messaging module 320 (FIG. 3) may alone or in conjunction with other software be used to transmit the medical information to the medical facility.

Figure 15:
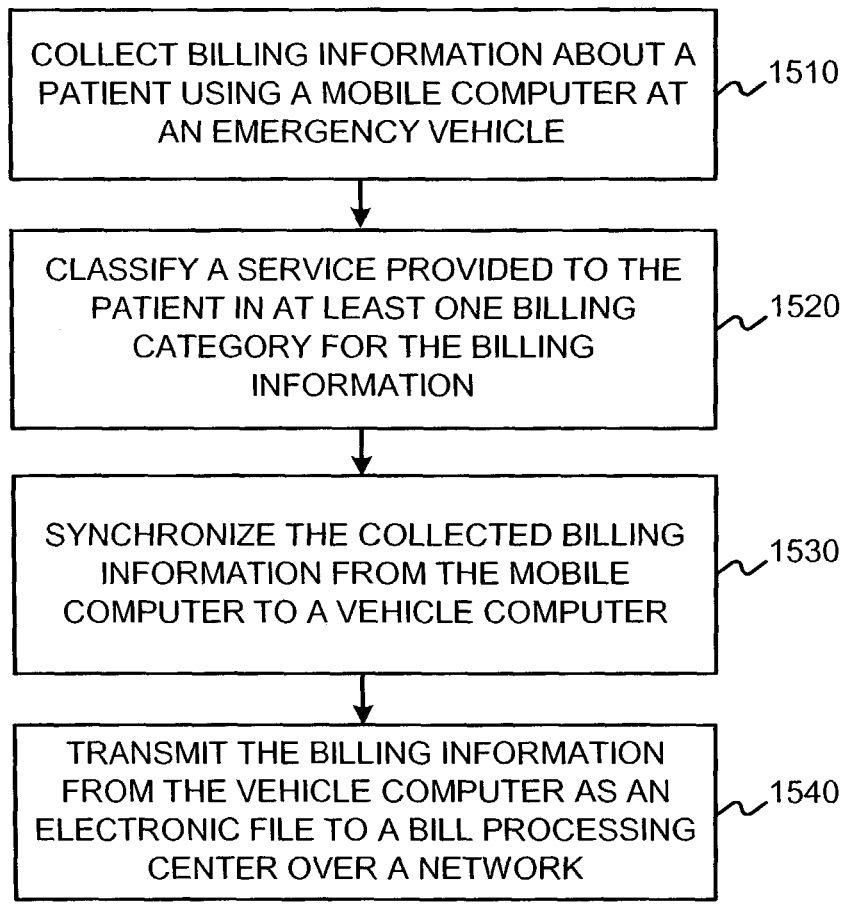
FIG. 15 is a flow diagram illustrating an exemplary method for processing billing information about a patient at an emergency vehicle consistent with the methods and systems of the present invention.

FIG. 15 is flow diagram illustrating an exemplary method for processing billing information about a patient at an emergency vehicle. The method may include collecting billing information about the patient using a mobile computer at the emergency vehicle (step 1510). The medical information may include at least one of a patient identification, a patient name, a patient address, and a billing code.

The method may further include classifying a service provided to the patient in at least one billing category for the billing information (step 1420). The method may also include synchronizing the collected billing information from the mobile computer to a vehicle computer (step 1430). The billing information may then be transmitted from the vehicle computer as an electronic file to a bill processing center over a network. Messaging module 320 (FIG. 3) may alone or in conjunction with other software be used to transmit the billing information to the bill processing center.

Further, the method for processing billing information may include generating an automatic bill based on the billing information at the bill processing center. The bill may include at least one of a type of service rendered, a name of physician, and a type of coverage. The bill may further include at least one of a bill status and a payment status.

Other modifications and embodiments of the invention will be apparent to those skilled in the art from consideration of the specification and practice of the invention disclosed herein. For example, although embodiments of the invention have been described herein with reference to a vehicle, such as an emergency vehicle, they apply to any environment related to collection and transmission of information from a remote location to a central location.

What is claimed is:
1. A method for collecting information about a patient, comprising:
receiving, via a vehicle computer aboard an emergency vehicle located in a coverage area of a network, a request regarding the patient, wherein the request includes a dispatch order, and the vehicle computer includes a GPS and online mapping module for displaying a position of the emergency vehicle relative to an emergency scene;

collecting, via a mobile computer at the emergency vehicle, medical and billing information about the patient;

synchronizing, via the vehicle computer aboard the emergency vehicle, the collected medical and billing information with the received request regarding the patient to generate a synchronized medical and billing report;

after the emergency vehicle travels outside of the coverage area of the network, determining, by the vehicle computer aboard the emergency vehicle, whether the emergency vehicle has re-entered the coverage area of the network;

in response to determining that the emergency vehicle has entered the coverage area of the network, automatically transmitting, from the vehicle computer to a computing device at a medical facility and a computing device at a bill processing center over the network, the synchronized medical and billing report, wherein the synchronized medical and billing report includes data for the dispatch order, patient name, patient address, present condition, past history, care events, and findings;

outputting, via an output device at the medical facility, at least a portion of the medical and billing report before the patient arrives for treatment;

entering, by the computer in the bill processing center, the data contained in the synchronized medical and billing report into a billing database;

identifying, by the computer in the bill processing center, at least one billable item of a service or medication used on the patient based on the data contained in the synchronized medical and billing report;

determining whether the billing database contains sufficient information for generating a bill for the at least one billable item;

based on a determination that the billing database does not contain sufficient information for generating the bill, sending, from the bill processing center, a first notice to the patient to collect additional medical and billing information about the patient, including a type of health coverage the patient has, the additional medical and billing information being not previously contained in the billing database;

verifying, at the bill processing center, health coverage information for the patient received via the mobile computer aboard the emergency vehicle;

sending, from the bill processing center, a second notice to the patient based on the response to the first notice;

preparing, at the bill processing center, a bill for the patient, wherein the bill includes a fee related to the dispatch order; and sending, from the bill processing center, the bill to the patient at the patient address.

2. The method of claim 1, wherein the medical facility is a hospital.

3. The method of claim 2, further comprising:
receiving the synchronized medical and billing report at the hospital on a computer system.

4. The method of claim 3, wherein the computer system includes at least one of a computer, a network interface, an infrared port, and a printer.

5. The method of claim 1, wherein the synchronized medical and billing report is transmitted from the vehicle computer to the medical facility and the bill processing center over a redundant network.

6. The method of claim 5, wherein the redundant network is a wide-area network.

7. The method of claim 1, further comprising:
outputting the billing information at the bill processing center for automatic billing.

8. The method of claim 7, wherein the automatic billing is at least for the request regarding the patient.

9. The method of claim 1, wherein the mobile computer is a handheld computer.

10. The method of claim 1, wherein the mobile computer is a palm computer.

11. The method of claim 1, wherein the mobile computer is a field computer.

12. The method of claim 1, wherein the network is a Motorola radio frequency network.

13. A system for collecting information about a patient, comprising:

a messaging hardware module configured to receive, via a vehicle computer aboard an emergency vehicle located in a coverage area of a network, a request regarding the patient, wherein the request includes a dispatch order;

a GPS and online mapping module for displaying a position of the emergency vehicle relative to an emergency scene;

an information collection hardware module configured to collect medical and billing information about the patient using a mobile computer at the emergency vehicle;

an information delivery hardware module of the vehicle computer aboard the emergency vehicle, wherein the information delivery hardware module is configured to synchronize the collected medical and billing information with the received request regarding the patient to generate a synchronized medical and billing report;

wherein the messaging hardware module is further configured to, after the emergency vehicle travels outside of the coverage area of the network, determine whether the emergency vehicle has re-entered the coverage area of the network and, in response to determining that the emergency vehicle has entered the coverage area of the network, automatically transmit over the network the synchronized medical and billing report from the vehicle computer to a computing device at a medical facility and a computing device at a bill processing center, wherein the synchronized medical and billing report includes data for the dispatch order, patient name, patient address, present condition, past history, care events, and findings;

an information management hardware module configured to output, via an output device, at least a portion of the medical and billing report at the medical facility before the patient arrives for treatment, enter the data contained in the synchronized medical and billing report into a billing database, and identify at least one billable item of a service or medication used on the patient based on the data contained in the synchronized medical and billing report;

a notification module, at the bill processing center, configured to determine whether the billing database contains sufficient information for generating a bill for the at least one billable item, and based on a determination that the billing database does not contain sufficient information for generating the bill, send a first notice to the patient to collect additional medical and billing information about the patient, including a type of health coverage the patient has, verify health coverage information for the patient received via the vehicle computer aboard the emergency vehicle, and send a second notice to the patient based on the response to the first notice, the additional medical and billing information being not previously contained in the billing database;

a billing hardware module of the computing device at the bill processing center configured to prepare a bill for the patient, wherein the bill includes a fee related to the dispatch order; and a sending hardware module of the computing device at the bill processing center configured to send the bill to the patient at the patient address.

14. The system of claim 13, wherein the medical facility is a hospital.

15. The system of claim 14, further comprising:
an information management hardware module for receiving the medical information at the hospital on a computer system.

16. The system of claim 15, wherein the computer system includes at least one of a computer, a network interface, an infrared port, and a printer.

17. The system of claim 13, wherein the synchronized medical and billing report is transmitted from the vehicle computer to the medical facility and the bill processing center over a redundant network.

18. The system of claim 17, wherein the redundant network is a wide-area network.

19. The system of claim 13, further comprising:
a bill processing hardware module for outputting the billing information at a billing service for automatic billing.

20. The system of claim 19, wherein the automatic billing is at least for the request regarding the patient.

21. The system of claim 13, wherein the mobile computer is a handheld computer.

22. The system of claim 13, wherein the mobile computer is a palm computer.

23. The system of claim 13, wherein the mobile computer is a field computer.

24. The system of claim 13, wherein the network is a Motorola radio frequency network.

25. A non-transitory computer-readable medium containing instructions for a method for collecting information about a patient, the method comprising:
receiving, via a vehicle computer aboard an emergency vehicle located in a coverage area of a network, a request regarding the patient, wherein the request includes a dispatch order, and the vehicle computer includes a GPS and online mapping module for displaying a position of the emergency vehicle relative to an emergency scene;
collecting, using a mobile computer at the emergency vehicle, medical and billing information about the patient;
synchronizing, via the vehicle computer aboard the emergency vehicle, the collected medical and billing information with the received request regarding the patient to generate a synchronized medical and billing report;
after the emergency vehicle travels outside of the coverage area of the network, determining, by the vehicle computer aboard the emergency vehicle, whether the emergency vehicle has re-entered the coverage area of the network;
in response to determining that the emergency vehicle has entered the coverage area of the network, automatically transmitting, from the vehicle computer to a computing device at a medical facility and a computing device at a bill processing center over the network, the synchronized medical and billing report, wherein the synchronized medical and billing report includes data for the dispatch order, patient name, patient address, present condition, past history, care events, and findings;
outputting, via an output device at the medical facility, at least a portion of the medical and billing report before the patient arrives for treatment;
entering, by the computer in the bill processing center, the data contained in the synchronized medical and billing report into a billing database;
identifying, by the computer in the bill processing center, at least one billable item of a service or medication used on the patient based on the data contained in the synchronized medical and billing report;
determining whether the billing database contains sufficient information for generating a bill for the at least one billable item;
based on a determination that the billing database does not contain sufficient information for generating the bill, sending, from the bill processing center, a first notice to the patient to collect additional medical and billing information about the patient, including a type of health coverage the patient has, the additional medical and billing information being not previously contained in the billing database;
verifying, at the bill processing center, health coverage information for the patient received via the mobile computer aboard the emergency vehicle;
sending, from the bill processing center, a second notice to the patient based on the response to the first notice;
preparing, at the bill processing center, a bill for the patient, wherein the bill includes a fee related to the dispatch order; and
sending, from the bill processing center, the bill to the patient at the patient address.

26. A method for processing medical and billing information about a patient, comprising:
collecting, via a mobile computer at an emergency vehicle located in a coverage area of a network, information about the patient, wherein the information includes medical and billing information;
classifying, via the mobile computer, a service provided to the patient in at least one medical category for the medical information;
transmitting, from the mobile computer, the medical information to a vehicle computer aboard the emergency vehicle, and the vehicle computer includes a GPS and online mapping module for displaying a position of the emergency vehicle relative to an emergency scene;
synchronizing, at the vehicle computer, the collected information about the patient with a dispatch request regarding the patient to generate a synchronized medical and billing report, wherein the synchronized medical and billing report includes data for a dispatch order, patient name, patient address, present condition, past history, care events, and findings;
classifying, via the mobile computer, a service provided to the patient in at least one billing category for the billing information;
transmitting, from the mobile computer, the billing information to the vehicle computer;
after the emergency vehicle travels outside of the coverage area of the network, determining, by the vehicle computer, whether the emergency vehicle has re-entered the coverage area of the network;
in response to determining that the emergency vehicle has entered the coverage area of the network, automatically transmitting, from the vehicle computer to a computing device at a medical facility, the medical information as a first electronic file, wherein the first electronic file includes fields for patient name, present condition, past history, care events, and findings;

transmitting, from the vehicle computer to a bill processing center, the billing information as a second electronic file, wherein the second electronic file includes a field for the dispatch order;

outputting, via an output device at the medical facility, at least a portion of the medical information before the patient arrives for treatment;

entering, by the computer in the bill processing center, the data contained in the synchronized medical and billing report into a billing database;

identifying, by the computer in the bill processing center, at least one billable item of a service or medication used on the patient based on the data contained in the synchronized medical and billing report;

determining whether the billing database contains sufficient information for generating a bill for the at least one billable item;

based on a determination that the billing database does not contain sufficient information for generating the bill, sending, from the bill processing center, a first notice to the patient to collect additional medical and billing information about the patient, including a type of health coverage the patient has;

verifying, at the bill processing center, health coverage information for the patient received via the mobile computer aboard the emergency vehicle;

sending, from the bill processing center, a second notice to the patient based on the response to the first notice;

preparing, at the bill processing center, a bill for the patient, wherein the bill includes a fee related to the dispatch order; and sending, from the bill processing center, the bill to the patient at the patient address.

27. The method of claim 26, wherein the additional information concerning the type of health coverage the patient includes Medicare, Medicaid, or health insurance.

28. The method of claim 26, further comprising:
generating at least one of a client report, government report, and other report based on the billing information.

29. A system for processing medical and billing information about a patient, comprising:
an information collection hardware module, wherein the information collection hardware module is configured to collect information about the patient using a mobile computer at an emergency vehicle located in a coverage area of a network, wherein the information includes medical and billing information, for classifying a service provided to the patient in at least one medical category for the medical information, and for classifying a service provided to the patient in at least one billing category for the billing information;

a synchronization hardware module configured to synchronize the collected information about the patient with a dispatch request regarding the patient to generate a synchronized medical and billing report, wherein the synchronized medical and billing report includes fields for the dispatch order, patient name, patient address, present condition, past history, care events, and findings;

an information transfer hardware module, wherein the information transfer module is configured to transmit the medical and billing information from the mobile computer to a vehicle computer aboard the emergency vehicle;

a GPS and online mapping module for displaying a position of the emergency vehicle relative to an emergency scene;

an information delivery hardware module, wherein the information delivery module is configured to, after the emergency vehicle travels outside of the coverage area of the network, determine whether the emergency vehicle has re-entered the coverage area of the network and, in response to determining that the emergency vehicle has entered the coverage area of the network, automatically transmit the medical information as a first electronic file from the vehicle computer to a computing device at a medical facility, and automatically transmit the billing information as a second electronic file from the vehicle computer to a bill processing center, wherein the first electronic file includes data for patient name, present condition, past history, care events, and findings, and wherein the second electronic file includes a field for the dispatch order;

an information management hardware module at the medical facility, wherein the information management module is configured to output at least a portion of the medical information via an output device at the medical facility before the patient arrives for treatment, enter the data contained in the synchronized medical and billing report into a billing database, and identify at least one billable item of a service or medication used on the patient based on the data contained in the synchronized medical and billing report;

a notification hardware module, at the bill processing center, configured to determine whether the billing database contains sufficient information for generating a bill for the at least one billable item, and based on a determination that the billing database does not contain sufficient information for generating the bill, send a first notice to the patient to collect additional medical and billing information about the patient, including a type of health coverage the patient has, verify health coverage information for the patient received via the vehicle computer aboard the emergency vehicle, and send a second notice to the patient based on the response to the first notice;

a billing hardware module configured to prepare, at the bill processing center, a bill for the patient, wherein the bill includes a fee related to the dispatch order; and a sending hardware module configured to send, from the bill processing center, the bill to the patient at the patient address.

30. The system of claim 29, wherein the additional information concerning the type of health coverage the patient has includes Medicare, Medicaid, or health insurance.

31. The system of claim 29, further comprising:
a bill processing hardware module configured to generate at least one of a client report, government report, and other report based on the billing information.

32. A non-transitory computer-readable medium containing instructions for a method for processing medical and billing information about a patient, the method comprising:
collecting, using a mobile computer at an emergency vehicle located in a coverage area of a network, information about the patient, wherein the information includes medical and billing information;

classifying a service provided to the patient in at least one medical category for the medical information;

transmitting, to a vehicle computer aboard the emergency vehicle, the medical information, and the vehicle computer includes a GPS and online mapping module for displaying a position of the emergency vehicle relative to an emergency scene;

synchronizing, at the vehicle computer, the collected information about the patient with a dispatch request regarding the patient to generate a synchronized medical and billing report, wherein the synchronized medical and billing report includes data for a dispatch order, patient name, patient address, present condition, past history, care events, and findings;

classifying a service provided to the patient in at least one billing category for the billing information;

transmitting, to the vehicle computer, the billing information;

after the emergency vehicle travels outside of the coverage area of the network, determining, by the vehicle computer, whether the emergency vehicle has re-entered the coverage area of the network;

in response to determining that the emergency vehicle has entered the coverage area of the network, automatically transmitting, from the vehicle computer to a computing device at a medical facility, the medical information as a first electronic file, wherein the first electronic file includes fields for patient name, present condition, and past history;

transmitting, from the vehicle computer to a bill processing center, the billing information as a second electronic file, wherein the second electronic file includes a field for the dispatch order;

outputting, via an output device at the medical facility, at least a portion of the medical information before the patient arrives for treatment;

entering, by the computer in the bill processing center, the data contained in the synchronized medical and billing report into a billing database;

identifying, by the computer in the bill processing center, at least one billable item of a service or medication used on the patient based on the data contained in the synchronized medical and billing report;

determining whether the billing database contains sufficient information for generating a bill for the at least one billable item;

based on a determination that the billing database does not contain sufficient information for generating the bill, sending, from the bill processing center, a first notice to the patient to collect additional medical and billing information about the patient, including a type of health coverage the patient has;

verifying, at the bill processing center, health coverage information for the patient received via the mobile computer aboard the emergency vehicle;

sending, from the bill processing center, a second notice to the patient based on the response to the first notice;

preparing, at the bill processing center, a bill for the patient, wherein the bill includes a fee related to the dispatch order; and sending the bill to the patient at the patient address.

* * * * *